United States Patent [19]
Tsien et al.

[11] Patent Number: 5,925,558
[45] Date of Patent: Jul. 20, 1999

[54] ASSAYS FOR PROTEIN KINASES USING FLUORESCENT PROTEIN SUBSTRATES

[75] Inventors: Roger Y. Tsien, La Jolla; Andrew B. Cubitt, San Diego, both of Calif.

[73] Assignee: The Regents of the University of California, Oakland, Calif.

[21] Appl. No.: 08/680,876

[22] Filed: Jul. 16, 1996

[51] Int. Cl.$^6$ ............................. C12N 15/62; C12N 1/21; C07K 19/00
[52] U.S. Cl. ...................... 435/252.3; 435/325; 435/440; 435/320.1; 536/23.1; 536/23.4
[58] Field of Search ................................. 536/23.4, 23.1; 435/252.3, 320.1, 172.3, 325, 440

[56] References Cited

U.S. PATENT DOCUMENTS

| | | | |
|---|---|---|---|
| 4,314,936 | 2/1982 | Yaron et al. | 260/112.5 R |
| 5,264,563 | 11/1993 | Huse | 536/25.3 |
| 5,491,084 | 2/1996 | Chalfie | 435/189 |
| 5,599,906 | 2/1997 | Dasmahapartra | 530/350 |
| 5,602,021 | 2/1997 | Davis et al. | 435/211 |
| 5,605,809 | 2/1997 | Komoriya et al. | 435/23 |
| 5,614,191 | 3/1997 | Puri et al. | 424/178.1 |
| 5,625,048 | 4/1997 | Tsien et al. | 536/23.4 |

FOREIGN PATENT DOCUMENTS

| | | | |
|---|---|---|---|
| 0 428 000 A1 | 5/1991 | European Pat. Off. | |
| 91/01305 | 2/1991 | WIPO | |
| WO 91/01305 | 2/1991 | WIPO | C07D 13/00 |
| WO 94/28166 | 8/1994 | WIPO | C12Q 1/37 |
| WO 94/28166 | 12/1994 | WIPO | |
| WO 94/28173 | 12/1994 | WIPO | |
| WO 95/07463 | 3/1995 | WIPO | G01N 35/53 |
| WO 95/21191 | 8/1995 | WIPO | C07K 14/435 |
| WO 96/13607 | 5/1996 | WIPO | |
| WO 96/23810 | 8/1996 | WIPO | C07H 21/04 |
| WO 96/23898 | 8/1996 | WIPO | |
| WO/96/23810 | 8/1996 | WIPO | |
| WO 96/27027 | 9/1996 | WIPO | |
| WO 96/27675 | 9/1996 | WIPO | |
| WO 97/11094 | 3/1997 | WIPO | |
| WO 97/28261 | 8/1997 | WIPO | |

OTHER PUBLICATIONS

D.A. Malencik et al., "Characterization of a Fluorescent Substrate for the Adenosine 3'5'–Cyclic Monophosphate–Dependent Protein Kinase", Analytical Biochemistry 132(1): 34–40 Jul. 1983.
D.E. Wright et al., "Fluorometric Assay for Adenosine 3'5'–Cyclic Monophosphate–Dependent Protein Kniase and Phosphoprotein Phosphatase Activities", Proc. natl. Acad. Sci. 78(10): 6048–6050, Oct., 1981.
Z.H. Zhao et al., "Characterization of a New Substrate for Protein Kinase C: Assay by Continous Fluorometric Monitoring and High Performance Kiquid Chromotography", Biochem. Biophys. Res. Commun. 176(3): 1454–1461, May, 1991.
G. Sala–Newby et al., "Engineering a Bioluminescent Indicator for Cyclic AMP–Dependent Protein Kinase", Biochemical Journal 279: 727–732, Nov., 1991.

Prasher, D.C., et al. (1992) "Primary structure of the *Aequorea victoria* green–fluorescent protein", *Gene*, 111:229–233.
Chalfie, M., et al. (1994) "Green fluorescent protein as a marker for gene expression", *Science*, 263:802–805.
Cubitt, A.B., et al. (1995) "Understanding, improving and using green fluorescent proteins", *TIBS* 20:448–455.
Heim, R., et al. (1994) "Wavelength mutations and post-translational autoxidation of green fluorescent protein", *Proc. Natl. Acad. Sci. USA*, 91:12501–12504.
Heim, R., et al. (1995) "Improved green fluorescence", *Nature*, 373:663–665.
Kemp, B.E., et al. (1990) "Protein kinase recognition sequence motifs", *Trends Biochem. Sci.*, 15:342–346.
Songyang, Z., et al. (1994) "Use of an oriented peptide library to determine the optimal substrates of protein kinases", *Current Biology*, 4:973–982.
Colbran, et al. (1992) "A Phenylalanine in Peptide Substrates Provides for Selectivity between cGMP and cAMP––dependent Protein Kinases", *J. Biol. Chem.*, 267:9589–9594.
Graff, et al. (1991) "Protein Kinase C Substrate and Inhibitor Characteristics of Peptides Derived from the Myristiylated Alanine–rich C Kinase Substrate (MARCKS) Protein Phosphorylation Site Domain", *J. Biol. Chem.*, 266:14390–14398.
Lee, et al. (1994) "A requirement of hydrophobic and basic amino acid residues for substrate recognition by $Ca^2$ / calmodulin–dependent protein kinase Ia", *Proc. Natl. Acad. Sci. USA*, 91:6413–6417.
Stokoe, et al. (1993) "The substrate specificity and structure of mitogen–activated protein (MAP) kinase–activated protein kinase–2", *Biochem. J.*, 296:843–849.
Cheng, Linzhao, et al. (1996) "Use of green fluorescent protein variants to monitor gene transfer and expression in mammalian cells", *Nature Biotechnology*, 14:606–609.
Heim, Roger, et al. (1996) "Engineering green fluorescent protein for improved brightness, longer wavelengths and fluorescence resonance energy transfer", *Current Biology*, 6(2):178–182.
Inouye and Tsuji, "Expression of the gene and fluorescence characteristics of the recombinant protein," *FEBS Letters* 341:277–280 (1994).
Baldwin et al., Biochemistry 29:5509–9915 (1990).
Blondel eta l., Protein Engineering 4:457–461 (1991).
Bouvier et al., Methods Enzymol. 248:614 (1995).
Cartwright et al., Yeast 10:497–508 (1994).
Cody et al., Biochemistry 32:1212–1218 (1993).
Delagrave et al., Bio/Technology 13:151–154 (1995).
Deschamps et al, Protein Expression and Purification, 6:555–558 (1995).

(List continued on next page.)

*Primary Examiner*—Rebecca E. Prouty
*Attorney, Agent, or Firm*—Fish & Richardson P.C.

[57] ABSTRACT

This invention provides assays for protein kinase activity using fluorescent proteins engineered to include sequences that can be phosphorylated by protein kinases. The proteins exhibit different fluorescent properties in the non-phosphorylated and phosphorylated states.

23 Claims, 14 Drawing Sheets

OTHER PUBLICATIONS

Dunn et al., Meth. Enzymol. 241:254 (1994)
Ehrig et al., FEBS Letters 367:163–166 (1995).
Hardy et al., Amyloid protein precursor in development, aging, and Alzheimer's disease ed., C.L. Masters et al, pp. 190–198 (1994).
Kain et al., BioTechniques 19:650–655 (1995).
Knight, Methods Enzymol., 248:18–34 (1995).
Krafft et al., Methods Enzymol., 241:70–86 (1994).
Levine et al., Comp. Biochem. Physiol. 728:77–85 (1982).
Matayoshi et al., Science 247:954 (1990).
Mitra et al., Gene, 173:13–17 (1996).
Muhlrad et al., Yeast 8:79–82 (1992).
Norris et al., Plant Molecular Biology, 24:673–677 (1994).
Seidah et al., Methods Enzymol., 244:175 (1994).
Smith et al., Methods Enzymol., 244:412 (1994).
Stryer, Ann. Rev. Biochem. 47:819–846 (1978).
Surpin et al., Photochem. Photobiol. 49: Abstract, 25S (1989).
Thornberry, Methdods Enzymol., 244:614 (1994).
Tsien et al., Trends Cell. Biol., 3:242–245 (1993).
Ward, in Bioluminescence and Chemiluminescence (eds. DeLuca et al., 235–242 (Academic Press, New York, 1981).
Ward et al., Biochemistry 21:4535–4540 (1982).
Ward et al., Photochem. Photobiol. 35:803–808 (1982).
Wilbanks et al., J. Biol. Chem. 268:1226–1235 (1993).
Yaron et al., Analytical Biochem. 95:228–235 (1979).
Roth, Thesis from the Graduate Program in Biochemistry from Rutgers, the State University of New Jersey (Oct. 1985).

SEQ ID NO:1:
SEQ ID NO:2:

| | | | | | | | | | | | | | | | | |
|---|---|---|---|---|---|---|---|---|---|---|---|---|---|---|---|---|
| ATG | AGT | AAA | GGA | GAA | GAA | CTT | TTC | ACT | GGA | GTT | GTC | CCA | ATT | CTT | GTT | 48 |
| Met | Ser | Lys | Gly | Glu | Glu | Leu | Phe | Thr | Gly | Val | Val | Pro | Ile | Leu | Val | |
| 1 | | | | 5 | | | | | 10 | | | | | | 15 | |
| GAA | TTA | GAT | GGT | GAT | GTT | AAT | GGG | CAC | AAA | TTT | TCT | GTC | AGT | GGA | GAG | 96 |
| Glu | Leu | Asp | Gly | Asp | Val | Asn | Gly | His | Lys | Phe | Ser | Val | Ser | Gly | Glu | |
| | | | 20 | | | | | 25 | | | | | 30 | | | |
| GGT | GAA | GGT | GAT | GCA | ACA | TAC | GGA | AAA | CTT | ACC | CTT | AAA | TTT | ATT | TGC | 144 |
| Gly | Glu | Gly | Asp | Ala | Thr | Tyr | Gly | Lys | Leu | Thr | Leu | Lys | Phe | Ile | Cys | |
| | | 35 | | | | | 40 | | | | | 45 | | | | |
| ACT | ACT | GGA | AAA | CTA | CCT | GTT | CCA | TGG | CCA | ACA | CTT | GTC | ACT | ACT | TTC | 192 |
| Thr | Thr | Gly | Lys | Leu | Pro | Val | Pro | Trp | Pro | Thr | Leu | Val | Thr | Thr | Phe | |
| | 50 | | | | | 55 | | | | | 60 | | | | | |
| TCT | TAT | GGT | GTT | CAA | TGC | TTT | TCA | AGA | TAC | CCA | GAT | CAT | ATG | AAA | CGG | 240 |
| Ser | Tyr | Gly | Val | Gln | Cys | Phe | Ser | Arg | Tyr | Pro | Asp | His | Met | Lys | Arg | |
| 65 | | | | | 70 | | | | | 75 | | | | | 80 | |
| CAT | GAC | TTT | TTC | AAG | AGT | GCC | ATG | CCC | GAA | GGT | TAT | GTA | CAG | GAA | AGA | 288 |
| His | Asp | Phe | Phe | Lys | Ser | Ala | Met | Pro | Glu | Gly | Tyr | Val | Gln | Glu | Arg | |
| | | | 85 | | | | | 90 | | | | | 95 | | | |
| ACT | ATA | TTT | TTC | AAA | GAT | GAC | GGG | AAC | TAC | AAG | ACA | CGT | GCT | GAA | GTC | 336 |
| Thr | Ile | Phe | Phe | Lys | Asp | Asp | Gly | Asn | Tyr | Lys | Thr | Arg | Ala | Glu | Val | |
| | | 100 | | | | | 105 | | | | | 110 | | | | |
| AAG | TTT | GAA | GGT | GAT | ACC | CTT | GTT | AAT | AGA | ATC | GAG | TTA | AAA | GGT | ATT | 384 |
| Lys | Phe | Glu | Gly | Asp | Thr | Leu | Val | Asn | Arg | Ile | Glu | Leu | Lys | Gly | Ile | |
| | 115 | | | | | 120 | | | | | 125 | | | | | |

FIG. 3A

```
GAT TTT AAA GAA GAT GGA AAC ATT CTT GGA CAC AAA TTG GAA TAC AAC    432
Asp Phe Lys Glu Asp Gly Asn Ile Leu Gly His Lys Leu Glu Tyr Asn
130                     135                 140

TAT AAC TCA CAC AAT GTA TAC ATC ATG GCA GAC AAA CAA AAG AAT GGA    480
Tyr Asn Ser His Asn Val Tyr Ile Met Ala Asp Lys Gln Lys Asn Gly
145                     150                 155                 160

ATC AAA GTT AAC TTC AAA ATT AGA CAC AAC ATT GAA GAT GGA AGC GTT    528
Ile Lys Val Asn Phe Lys Ile Arg His Asn Ile Glu Asp Gly Ser Val
        165                 170                 175

CAA CTA GCA GAC CAT TAT CAA CAA AAT ACT CCA ATT GGC GAT GGC CCT    576
Gln Leu Ala Asp His Tyr Gln Gln Asn Thr Pro Ile Gly Asp Gly Pro
    180                 185                 190

GTC CTT TTA CCA GAC AAC CAT TAC CTG TCC ACA CAA TCT GCC CTT TCG    624
Val Leu Leu Pro Asp Asn His Tyr Leu Ser Thr Gln Ser Ala Leu Ser
195                 200                 205

AAA GAT CCC AAC GAA AAG AGA GAC CAG ATG GTC CTT CTT GAG TTT GTA    672
Lys Asp Pro Asn Glu Lys Arg Asp Gln Met Val Leu Leu Glu Phe Val
210                 215                 220

ACA GCT GGG ATT ACA CAT GGC ATG GAT GAA CTA TAC AAA TA             717
Thr Ala Gly Ile Thr His Gly Met Asp Glu Leu Tyr Lys
225                 230                 235
```

FIG. 3B

```
                                      20                    40                    60
                                       *                     *                     *
ATG AGT AAA GGA GAA GAA CTT TTC ACT GGA GTT GTC CCA ATT CTT GTT GAA TTA GAT GGT
Met Ser Lys Gly Glu Glu Leu Phe Thr Gly Val Val Pro Ile Leu Val Glu Leu Asp Gly
                             80                   100                   120
                        (His Lys)*                  *                     *
GAT GTT AAT GGG AGA AGA TTT TCT GTC AGT GGA GAG GGT GAT GCA ACA TAC GGA
Asp Val Asn Gly Arg Arg Phe Ser Val Ser Gly Glu Gly Asp Ala Thr Tyr Gly
               140                   160                   180
                 *                     *                     *
AAA CTT ACC CTT AAA TTT ATT TGC ACT ACT GGA AAA CTA CCT GTT CCA ACA CTT
Lys Leu Thr Leu Lys Phe Ile Cys Thr Thr Gly Lys Leu Pro Val Pro Thr Leu
               200                   220                   240
                 *        (Gln Cys)    (Arg)*                  *
GTC ACT ACT TTC TCT TAT GGT GTT AGA AGA TTT TCA GCA TAC CCA GAT CAT AGT AAA CAG
Val Thr Thr Phe Ser Tyr Gly Val Arg Arg Phe Ser Ala Tyr Pro Asp His Ser Lys Gln
                   260                   280                   300
                     *                     *  (Glu)              *
CAT GAC TTT TTC AAG AGT GCC ATG CCC GAA GGT TAT GTA CAG AGA AGA TCT ATA TTT TTC
His Asp Phe Phe Lys Ser Ala Met Pro Glu Gly Tyr Val Gln Arg Arg Ser Ile Phe Phe
                   320                   340                   360
                     *                     *                     *
AAA GAT GAC GGG AAC TAC AAG ACA CGT GCT GAA GTC AAG TTT GAA GGT GAT ACC CTT GTT
Lys Asp Asp Gly Asn Tyr Lys Thr Arg Ala Glu Val Lys Phe Glu Gly Asp Thr Leu Val
```

FIG. 4A

```
                    380                        400                         420
                     *             (Glu Asp)*   (Asn)                       *
AAT AGA ATC GAG TTA AAA GGT ATT GAT TTT AAA AGA AGA GGA AAC ATT CTT GGA CAC AAA
Asn Arg Ile Glu Leu Lys Gly Ile Asp Phe Lys Arg Arg Gly Asn Ile Leu Gly His Lys
                         440                        460                        480
                          *                          *              (Gln)(Asn)  *
TTG GAA TAC AAC TAT AAC TCA CAC AAT GTA TAC ATC ATG GCA GAC AAA GCA GAC AAG AGA AGA TCT GGA
Leu Glu Tyr Asn Tyr Asn Ser His Asn Val Tyr Ile Met Ala Asp Lys Ala Asp Lys Arg Arg Ser Gly
                    500                        520                        540
                     *              (Glu Asp)*                             *
ATC AAA GTT AAC TTC AAA ATT AGA CAC AAC ATT AGA AGA GGA AGC GTT CAA CTA GCA GAC
Ile Lys Val Asn Phe Lys Ile Arg His Asn Ile Arg Arg Gly Ser Val Gln Leu Ala Asp
                         560                        580                        600
                          *                          *                 (His Tyr)
CAT TAT CAA CAA AAT ACT CCA ATT GGC GAT GGC CCT GTC CTT TTA CCA GAC AAC AGA AGA
His Tyr Gln Gln Asn Thr Pro Ile Gly Asp Gly Pro Val Leu Leu Pro Asp Asn Arg Arg
                    620                        640                        660
(Thr)                *                          *                (His)     *
CTG TCC ATA CAA TCT GCC CTT TCG AAA GAT CCC AAC GAA AAG AGA GAC AAG AGA ATG GTC CTT
Leu Ser Ile Gln Ser Ala Leu Ser Lys Asp Pro Asn Glu Lys Arg Asp Lys Arg Met Val Leu
                         680                        700
                          *                          *
CTT GAG TTT GTA ACA GCT GCT GGG ATT ACA CAT GGC ATG GAT GAA CTA TAC AAA TAA
Leu Glu Phe Val Thr Ala Ala Gly Ile Thr His Gly Met Asp Glu Leu Tyr Lys ***
```

FIG. 4B

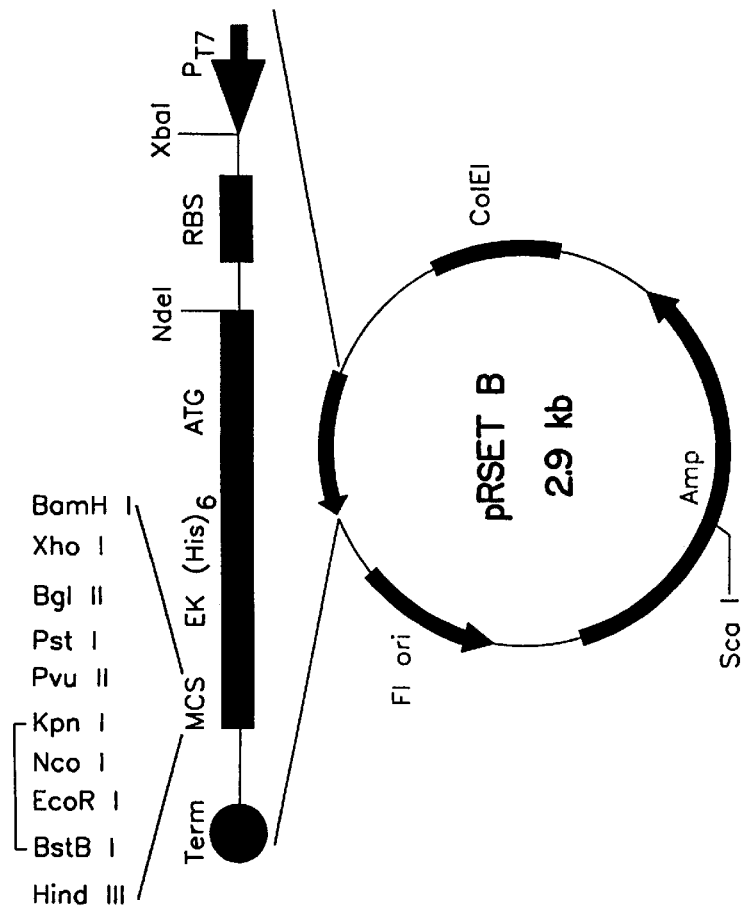
FIG. 5

ASSAYS FOR PROTEIN KINASES USING FLUORESCENT PROTEIN SUBSTRATES

BACKGROUND OF THE INVENTION

This invention relates to the field of enzymatic assays and, in particular, assays for protein kinase activity involving modified fluorescent proteins.

Protein phosphorylation is one of the most important general mechanisms of cellular regulation. Protein phosphorylation commonly occurs on three major amino acids, tyrosine, serine or threonine, and changes in the phosphorylation state of these amino acids within proteins can regulate many aspects of cellular metabolism, regulation, growth and differentiation. Changes in the phosphorylation state of proteins, mediated through phosphorylation by kinases, or dephosphorylation by phosphatases, is a common mechanism through which cell surface signaling pathways transmit and integrate information into the nucleus. Given their key role in cellular regulation, it is not surprising that defects in protein kinases and phosphatases have been implicated in many disease states and conditions. For example, the over-expression of cellular tyrosine kinases such as the EGF or PDGF receptors, or the mutation of tyrosine kinases to produce constitutively active forms (oncogenes) occurs in many cancer cells. Drucker et al. (1996) *Nature Medicine* 2: 561–56. Protein tyrosine kinases are also implicated in inflammatory signals. Defective Thr/Ser kinase genes have been demonstrated to be implicated in several diseases such as myotonic dystrophy as well as cancer, and Alzheimer's disease (Sanpei et al. (1995) *Biochem. Biophys. Res. Commun.* 212: 341–6; Sperber et al (1995) *Neurosci. Lett.* 197: 149–153; Grammas et al (1995) *Neurobiology of Aging* 16: 563–569; Govoni et al. (1996) *Ann. N.Y. Acad. Sci.* 777: 332–337).

The involvement of protein kinases and phosphatases in disease states makes them attractive targets for the therapeutic intervention of drugs, and in fact many clinically useful drugs act on protein kinases or phosphatases. Examples include cyclosporin A which is a potent immunosuppressant that binds to cyclophilin. This complex binds to the Ca/calmodulin-dependent protein phosphatase type 2B (calcineurin) inhibiting its activity, and hence the activation of T-cells. (Sigal and Dumont (1992), Schreiber and Crabtree (1992)). Inhibitors of protein kinase C are in clinical trails as therapeutic agents for the treatment of cancer. (*Clin. Cancer Res.* (1995) 1:113–122) as are inhibitors of cyclin dependent kinase. (*J. Mol. Med.* (1995) 73:(10):509–14.)

The number of known kinases and phosphatases are growing rapidly as the influence of genomic programs to identify the molecular basis for diseases have increased in size and scope. These studies are likely to implicate many more kinase and phosphatase genes in the development and propagation of diseases in the future, thereby making them attractive targets for drug discovery. However current methods of measuring protein phosphorylation have many disadvantages which prevents or limits the ability to rapidly screen using miniaturized automated formats of many thousands of compounds. This is because current methods rely on the incorporation and measurement of $^{32}P$ into the protein substrates of interest. In whole cells this necessitates the use of high levels of radioactivity to efficiently label the cellular ATP pool and to ensure that the target protein is efficiently labeled with radioactivity. After incubation with test drugs, the cells must be lysed and the protein of interest purified to determine its relative degree of phosphorylation. This method requires high numbers of cells, long preincubation times, careful manipulation and washing steps (to avoid artifactual phosphorylation or dephosphorylation), as well as a method of purification of the target protein. Furthermore, final radioactive incorporation into target proteins is usually very low, giving the assay poor sensitivity. Alternative assay methods, for example based on phosphorylation-specific antibodies using ELISA-type approaches, involve the difficulty of producing antibodies that distinguish between phosphorylated and non-phosphorylated proteins, and the requirement for cell lysis, multiple incubation and washing stages which are time consuming, complex to automate and potentially susceptible to artifacts.

Kinase assays based on purified enzymes require large amounts of purified kinases, high levels of radioactivity, and methods of purification of the substrate protein away from incorporated $^{32}P$-labelled ATP. They also suffer from the disadvantage of lacking the physiological context of the cell, preventing a direct assessment of a drugs toxicity and ability to cross the cells plasma membrane.

Fluorescent molecules are attractive as reporter molecules in many assay systems because of their high sensitivity and ease of quantification. Recently, fluorescent proteins have been the focus of much attention because they can be produced in vivo by biological systems, and can be used to trace intracellular events without the need to be introduced into the cell through microinjection or permeabilization. The green fluorescent protein of *Aequorea Victoria* is particularly interesting as a fluorescent indicator protein. A cDNA for the protein has been cloned. (D. C. Prasher et al., "Primary structure of the *Aequorea Victoria* green-fluorescent protein," *Gene* (1992) 111:229–33.) Not only can the primary amino acid sequence of the protein be expressed from the cDNA, but the expressed protein can fluoresce. This indicates that the protein can undergo the cyclization and oxidation believed to be necessary for fluorescence. The fluorescence of green fluorescent protein is generated from residues S65-Y66-G67.

Fluorescent proteins have been used as markers of gene expression, tracers of cell lineage and as fusion tags to monitor protein localization within living cells. (M. Chalfie et al., "Green fluorescent protein as a marker for gene expression," *Science* 263:802–805; A. B. Cubitt et al., "Understanding, improving and using green fluorescent proteins," *TIBS* 20, November 1995, pp. 448–455. U.S. Pat. No. 5,491,084, M. Chalfie and D. Prasher. Furthermore, mutant versions of green fluorescent protein have been identified that exhibit altered fluorescence characteristics, including altered excitation and emission maxima, as well as excitation and emission spectra of different shapes. (R. Heim et al., "Wavelength mutations and posttranslational autoxidation of green fluorescent protein," *Proc. Natl. Acad. Sci. USA*, (1994) 91:12501–04; R. Heim et al., "Improved green fluorescence," *Nature* (1995) 373:663–665.) These properties add variety and utility to the arsenal of biologically based fluorescent indicators.

There is a need for assays of protein phosphorylation that are simple, sensitive, non-invasive, applicable to living cells and tissues and that avoid the use of any radioactivity.

SUMMARY OF THE INVENTION

When fluorescent proteins are modified to incorporate a phosphorylation site recognized by a protein kinase, the fluorescent proteins not only can become phosphorylated by the protein kinase, but they also can exhibit different fluorescent characteristics in their un-phosphorylated and phosphorylated forms when irradiated with light having a wavelength within their excitation spectrum. This characteristic makes fluorescent protein substrates particularly useful for assaying protein kinase activity in a sample.

This invention provides methods for determining whether a sample contains protein kinase activity. The methods involve contacting the sample with a phosphate donor, usually ATP, and a fluorescent protein substrate of the invention; exciting the fluorescent protein substrate with light of an appropriate wavelength; and measuring the amount of a fluorescent property that differs in the un-phosphorylated state and phosphorylated state. An amount that is consistent with the presence of the fluorescent protein substrate in its phosphorylated state indicates the presence of protein kinase activity, and an amount that is consistent with the presence of the protein substrate in its un-phosphorylated state indicates the absence of protein kinase activity.

One embodiment of the above method is for determining the amount of protein kinase activity in a sample. In this method, measuring the amount of a fluorescent property in the sample comprises measuring the amount at two or more time points after contacting the sample with a phosphate donor and a fluorescent protein substrate of the invention, and determining the quantity of change or rate of change of the measured amount. The quantity or rate of change of the measured amount reflects the amount of protein kinase activity in the sample.

In another aspect, the invention provides methods for determining whether a cell exhibits protein kinase activity. The methods involve the steps of providing a transfected host cell of the invention that produces a fluorescent protein substrate of the invention; exciting the protein substrate in the cell with light of an appropriate wavelength; and measuring the amount of a fluorescent property that differs in the unphosphorylated and phosphorylated states. An amount that is consistent with the presence of the protein substrate in its phosphorylated state indicates the presence of protein kinase activity, and an amount that is consistent with the presence of the protein substrate in its un-phosphorylated state indicates the absence of protein kinase activity or the presence of phosphatase activity.

In another aspect, the invention provides methods for determining the amount of activity of a protein kinase in one or more cells from an organism. The methods involve providing a transfected host cell comprising a recombinant nucleic acid molecule comprising expression control sequences operatively linked to a nucleic acid sequence coding for the expression of a fluorescent protein substrate of the invention, the cell expressing the fluorescent protein substrate; exciting the protein substrate in the cell with light; and measuring the amount of a fluorescent property that differs in the unphosphorylated and phosphorylated states at two or more time points after contacting the sample with a phosphate donor and a fluorescent protein substrate, and determining the quantity or rate of change of the measured amount. The quantity or rate of change of the measured amount reflects the amount of protein kinase activity in the sample.

This invention also provides screening methods for determining whether a compound alters the activity of a protein kinase. The methods involve contacting a sample containing a known amount of protein kinase activity with the compound, a phosphate donor for the protein kinase and a fluorescent protein substrate of the invention; exciting the protein substrate; measuring the amount of protein kinase activity in the sample as a function of the quantity or rate of change of a fluorescent property that differs in the un-phosphorylated and phosphorylated states; and comparing the amount of activity in the sample with a standard activity for the same amount of the protein kinase. A difference between the amount of protein kinase activity in the sample and the standard activity indicates that the compound alters the activity of the protein kinase.

Another aspect of the drug screening methods involve determining whether a compound alters the protein kinase activity in a cell. The methods involve providing first and second transfected host cells exhibiting protein kinase activity and expressing a fluorescent protein substrate of the invention; contacting the first cell with an amount of the compound; contacting the second cell with a different amount of the compound; exciting the protein substrate in the first and second cells; measuring the amount of protein kinase activity as a function of the quantity of change or rate of change of a fluorescent property that differs in the un-phosphorylated and phosphorylated states in the first and second cells; and comparing the amount in the first and second cells. A difference in the amount indicates that the compound alters protein kinase activity in the cell.

This invention also provides fluorescent protein substrates for a protein kinase. Fluorescent protein substrates for a protein kinase comprise a fluorescent protein moiety and a phosphorylation site for a protein kinase. The protein substrate exhibits a different fluorescent property in the phosphorylated state than in the unphosphorylated state. In a preferred embodiment, the fluorescent protein is an Aequorea-related fluorescent protein. In another embodiment, the phosphorylation site is located within about 5, 10, 15 or 20 amino acids of a terminus, e.g., the amino-terminus, of the fluorescent protein moiety. In another embodiment, the protein substrate comprises the phosphorylation site more than 20 amino acids from a terminal of the fluorescent protein moiety and within the fluorescent protein moiety. The phosphorylation site can be one recognized by, for example, protein kinase A, a cGMP-dependent protein kinase, protein kinase C, $Ca^{2+}$/calmodulin-dependent protein kinase I, $Ca^{2+}$/calmodulin-dependent protein kinase II or MAP kinase activated protein kinase type 1.

This invention also provides nucleic acid molecules coding for the expression of a fluorescent protein substrate for a protein kinase of the invention. In one aspect, the nucleic acid molecule is a recombinant nucleic acid molecule comprising expression control sequences operatively linked to a nucleic acid sequence coding for the expression of a fluorescent protein substrate for a protein kinase of the invention. In another aspect, the invention provides transfected host cells transfected with a recombinant nucleic acid molecule comprising expression control sequences operatively linked to a nucleic acid sequence coding for the expression of a fluorescent protein substrate for a protein kinase of the invention.

In another aspect, this invention provides collections of fluorescent protein candidate substrates comprising at least 10 different members, each member comprising a fluorescent protein moiety and a variable peptide moiety around the terminus of the fluorescent protein moiety.

In another embodiment, the invention provides collections of recombinant nucleic acid molecules comprising at least 10 different recombinant nucleic acid molecule members, each member comprising expression control sequences operatively linked to nucleic acid sequences coding for the expression of a different fluorescent protein candidate substrate of the invention. The invention also provides collections of host cells comprising at least 10 different host cell members, each member comprising the above recombinant nucleic acid molecules.

The collections of cells are useful in determining the specificity of cellular kinases, from either diseased or normal tissues. The screening methods involve providing a collection of transfected host cells of the invention; culturing the collection of host cells under conditions for the expression of the fluorescent protein candidate substrate; and determining for each of a plurality of members from the collection whether the member contains a fluorescent protein candidate substrate that exhibits a fluorescent property different than the fluorescent property exhibited by the non-phosphorylated candidate substrate. The presence of fluorescent protein candidate substrate that exhibits a fluorescent property different than the fluorescent property exhibited by the candidate substrate indicates that the candidate substrate possesses a peptide moiety that can be phosphorylated by the kinase present in the host cells.

This invention also provides kits comprising a fluorescent protein substrate and a phosphate donor.

BRIEF DESCRIPTION OF THE DRAWINGS

FIG. 3 depicts the nucleotide sequence (SEQ ID NO:1) and deduced amino acid sequence (SEQ ID NO:2) of a wild-type Aequorea green fluorescent protein.

FIG. 4 provides a list of the positions and amino acid changes made for phosphorylation mutants made more than fifteen amino acids in the primary sequence from the N-terminus (nucleotide=SEQ ID NO:36; amino acid=SEQ ID NO:37), as compared to FIG. 3. Amino acids underlined represent the phosphorylation motif, amino acids in brackets represent wild type sequence at those positions.

FIG. 5 depicts plasmid pRSET containing a region encoding GFP that is fused in frame with nucleotides encoding an N-terminal polyhistidine tag (nucleotide=SEQ ID NO:38 and SEQ ID NO:40; amino acid=SEQ ID NO:39).

DETAILED DESCRIPTION OF THE INVENTION

I. METHODS FOR ASSAYING SAMPLES FOR PROTEIN KINASES

Figure 1:
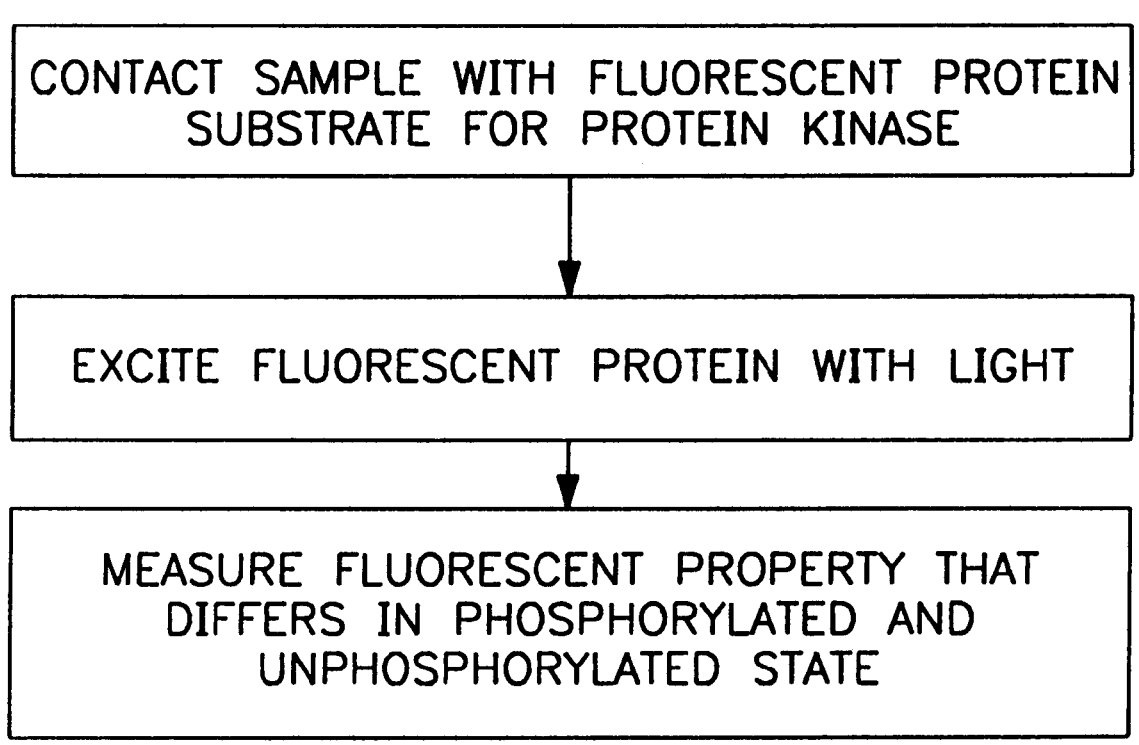
FIG. 1 is a flow chart showing the steps in an assay method for protein kinase activity.

Protein kinases add a phosphate residue to the phosphorylation site of a protein, generally through the hydrolysis of ATP to ADP. Fluorescent protein substrates for protein kinases are useful in assays to determine the amount of protein kinase activity in a sample. The assays of this invention take advantage of the fact that phosphorylation of the protein substrate results in a change in a fluorescent property of the fluorescent protein. Methods for determining whether a sample has kinase activity involve contacting the sample with a fluorescent protein substrate having a phosphorylation site recognized by the protein kinase to be assayed and with a phosphate donor under selected test conditions. A phosphate donor is a compound containing a phosphate moiety which the kinase is able to use to phosphorylate the protein substrate. ATP (adenosine-5'-triphosphate) is by far the most common phosphate donor. In certain instances, the sample will contain enough of a phosphate donor to make this step unnecessary. Then the fluorescent protein substrate is excited with light in its excitation spectrum. If the protein substrate has been phosphorylated, the substrate will exhibit different fluorescent properties, indicating that the sample contains protein kinase activity. For example, if the phosphorylated form of the protein substrate has higher fluorescence than the unphosphorylated form, the amount of fluorescence in the sample will increase as a function of the amount of substrate that has been phosphorylated. If the fluorescent property is a change in the wavelength maximum of emission, the change will be detected as a decrease in fluorescence at the wavelength maximum of the unphosphorylated substrate and an increase in fluorescence at the wavelength maximum of the phosphorylated substrate.

The amount of kinase activity in a sample can be determined by measuring the amount of a fluorescent property in the sample at a first time and a second time after contact between the sample, the fluorescent protein substrate and a phosphate donor, and determining the degree of change or the rate of change in a fluorescent property. For example, if phosphorylation results in an increase in fluorescence at the excitation wavelength maximum, the fluorescence of the substrate at this wavelength can be determined at two times. The amount of enzyme activity in the sample can be calculated as a function of the difference in the determined amount of the property at the two times. For example, the absolute amount of activity can be calibrated using standards of enzyme activity determined for certain amounts of enzyme after certain amounts of time. The faster or larger the difference in the amount, the more enzyme activity must have been present in the sample. The amount of a fluorescent property can be determined from any spectral or fluorescence lifetime characteristic of the excited substrate, for example, by determining the intensity of the fluorescent signal from the protein substrate or the excited state lifetime of the protein substrate, the ratio of the fluorescences at two different excitation wavelengths, the ratio of the intensities at two different emission wavelengths, or the excited lifetime of the protein substrate.

Fluorescence in a sample is measured using a fluorimeter. In general, excitation radiation from an excitation source having a first wavelength, passes through excitation optics. The excitation optics cause the excitation radiation to excite the sample. In response, fluorescent proteins in the sample emit radiation which has a wavelength that is different from the excitation wavelength. Collection optics then collect the emission from the sample. The device can include a temperature controller to maintain the sample at a specific temperature while it is being scanned. According to one embodiment, a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation. This process can be miniaturized and automated to enable screening many thousands of compounds.

Methods of performing assays on fluorescent materials are well known in the art and are described in, e.g., Lakowicz, J. R., *Principles of Fluorescence Spectroscopy*, New York:Plenum Press (1983); Herman, B., Resonance energy transfer microscopy, in: *Fluorescence Microscopy of Living Cells in Culture, Part B, Methods in Cell Biology*, vol. 30, ed. Taylor, D. L. & Wang, Y.-L., San Diego: Academic Press (1989), pp. 219–243; Turro, N.J., *Modern Molecular Photochemistry,* Menlo Park: Benjamin/ Cummings Publishing Col, Inc. (1978), pp. 296–361.

Enzymatic assays also can be performed on isolated living cells in vivo, or from samples derived from organisms transfected to express the substrate. Because fluorescent protein substrates can be expressed recombinantly inside a cell, the amount of enzyme activity in the cell or organism of which it is a part can be determined by determining a fluorescent property or changes in a fluorescent property of cells or samples from the organism.

Figure 2:
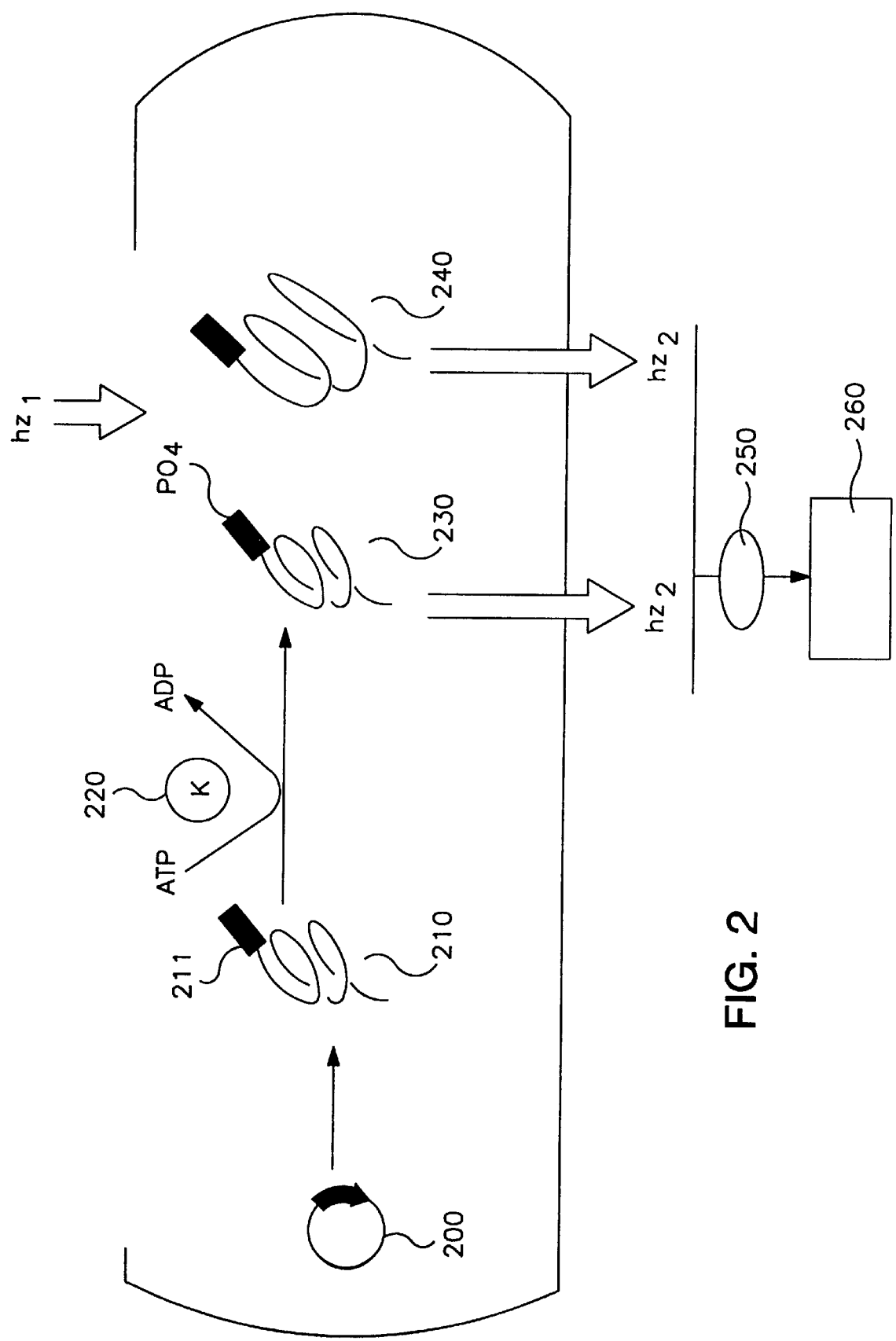
FIG. 2 depicts molecular events in a cell in altering and detecting fluorescent properties of a fluorescent protein substrate for a protein kinase.
Figure 6A:
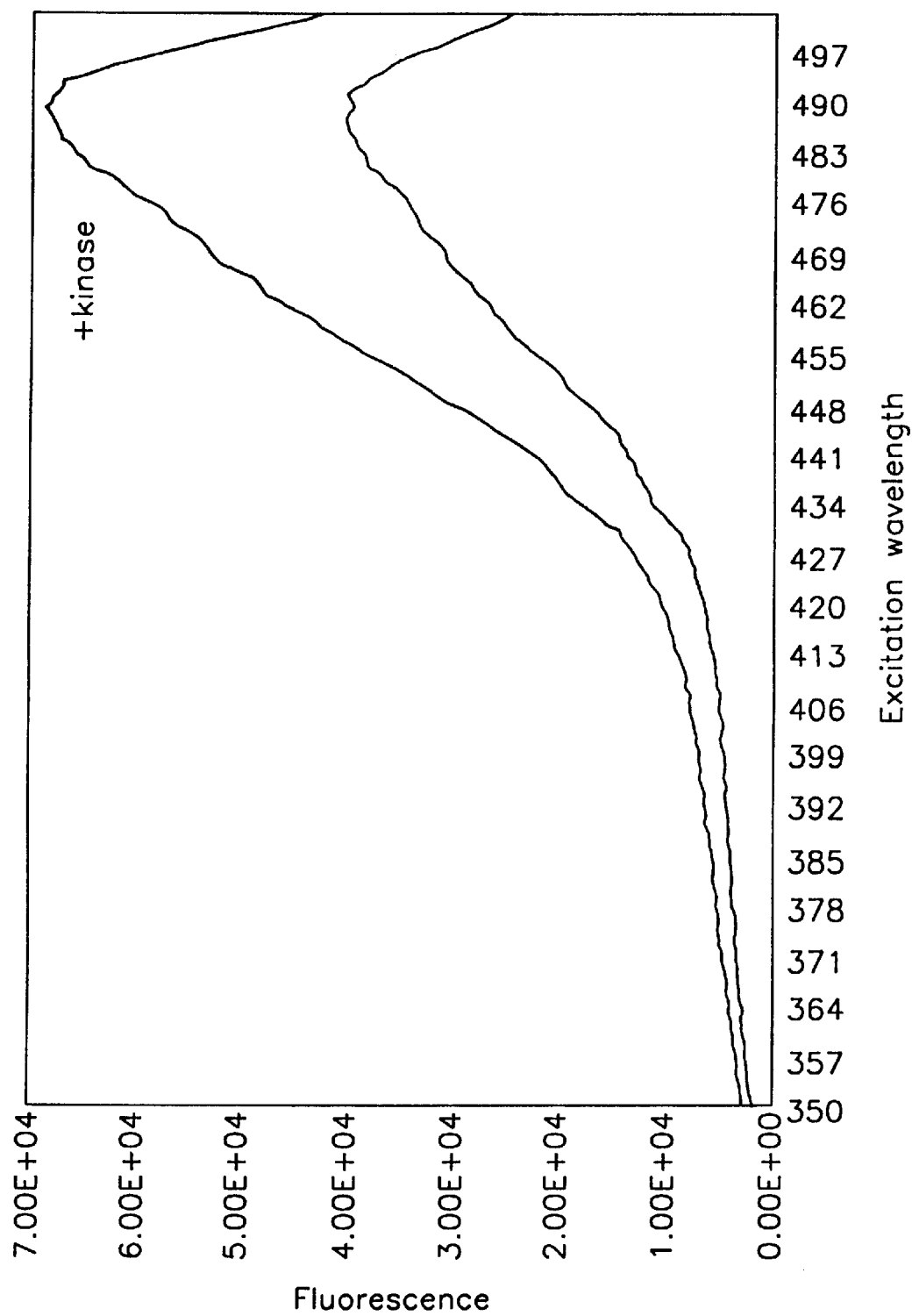
FIGS. 6A–6E show the fluorescence excitation spectra before and after phosphorylation of N-terminal phosphorylation mutants by protein kinase A using standard phosphorylation conditions. 6A: 1MSRRRRSI (SEQ ID NO:31). 6B: 1MRRRRSII (SEQ ID NO:32). 6C: -1MRRRRSIII (SEQ ID NO:33). 6D: -2MRRRRSIIIF (SEQ ID NO:34). 6E: -3MRRRRSIIIIF (SEQ ID NO:35). In all cases the spectrum after phosphorylation has higher amplitude than the spectrum before phosphorylation.
Figure 6B:
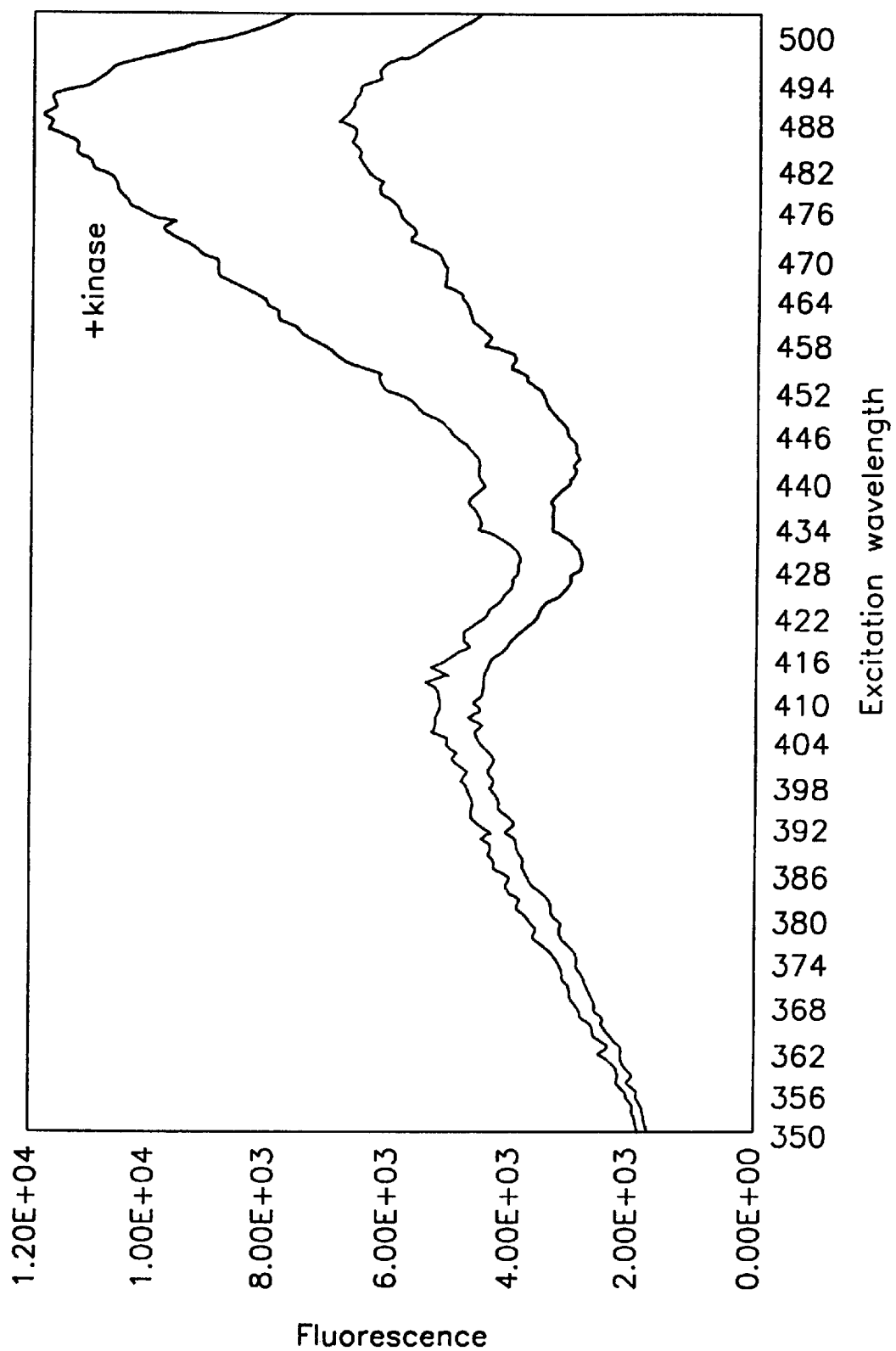
Figure 6C:
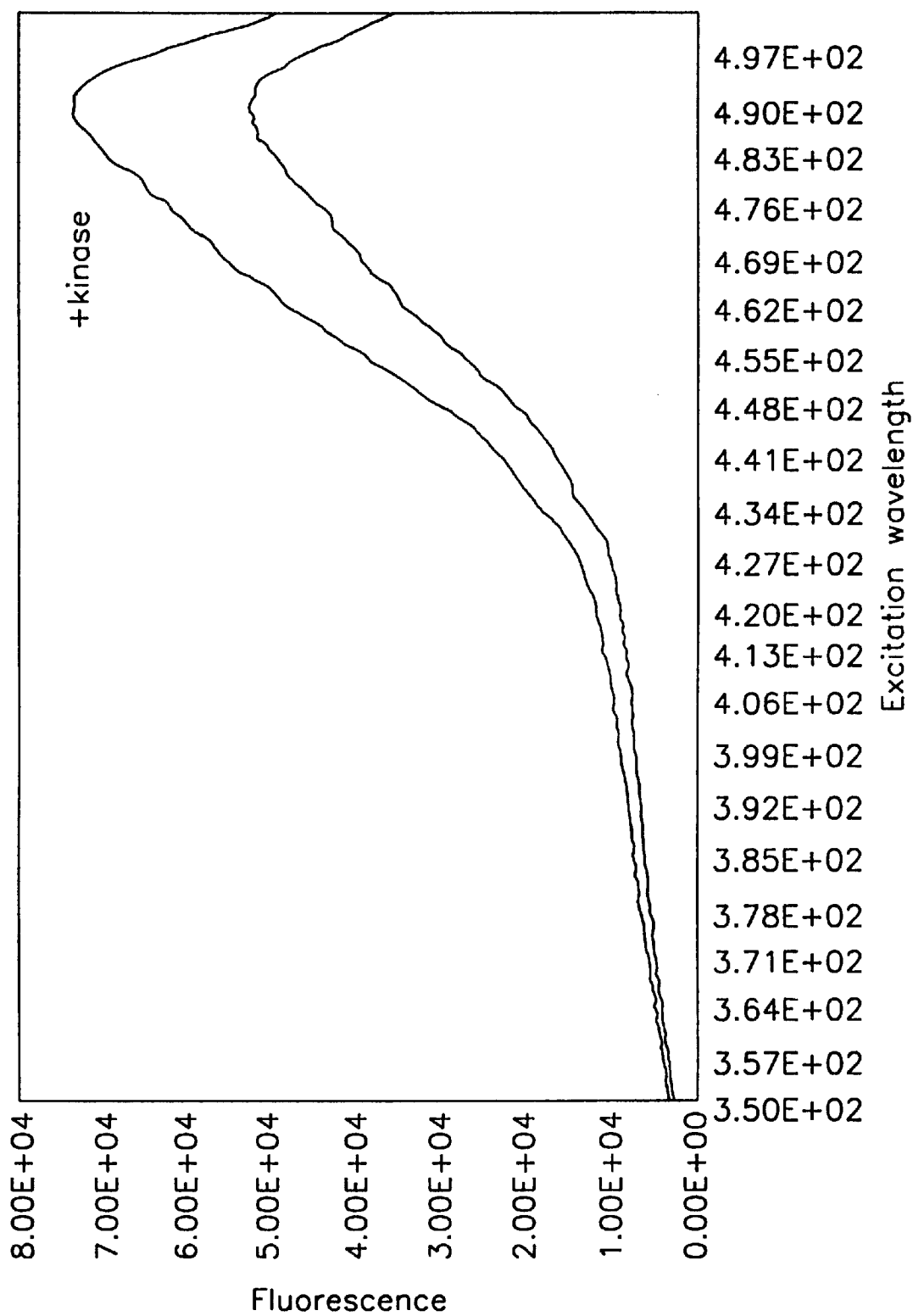
Figure 6D:
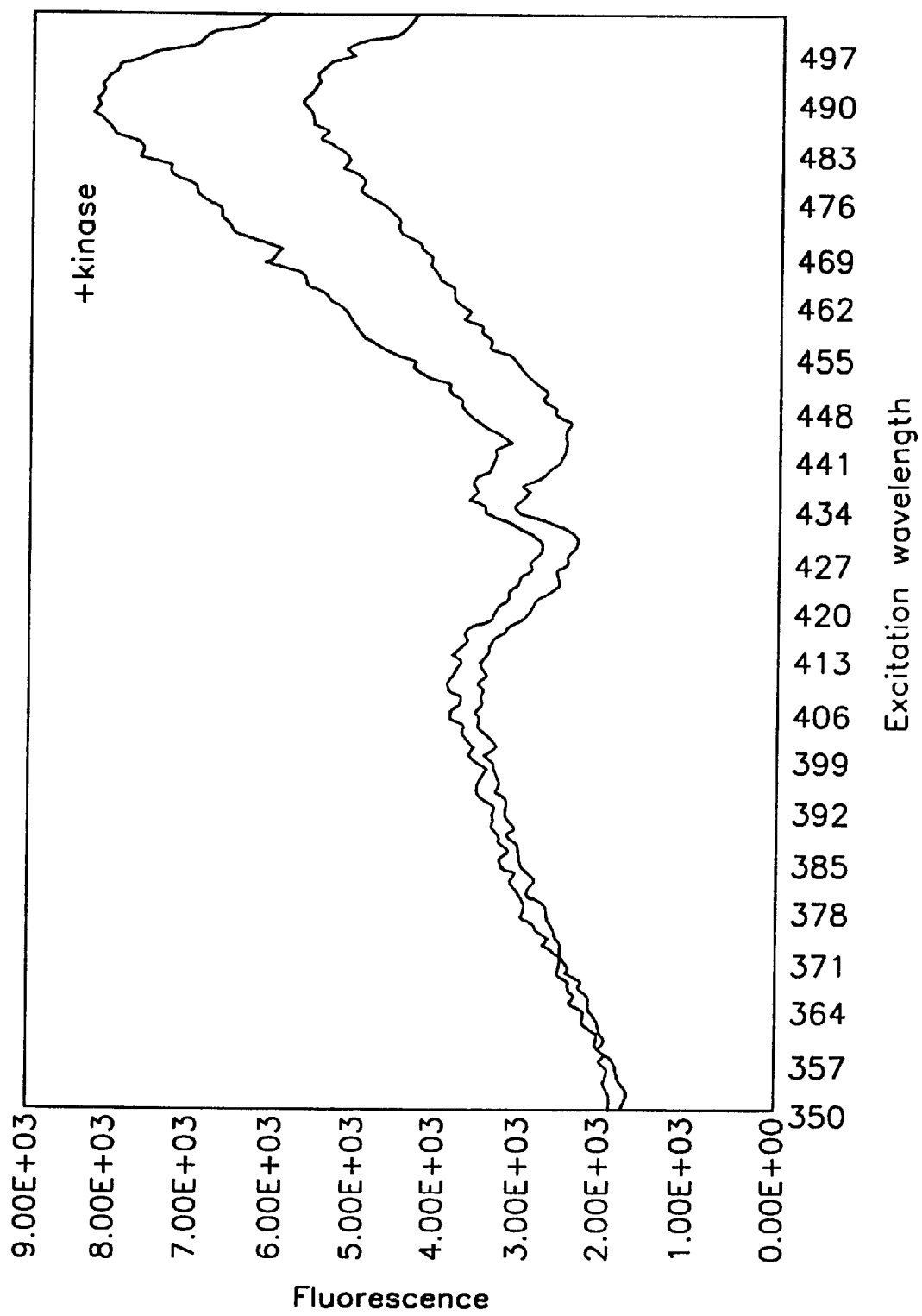
Figure 6E:
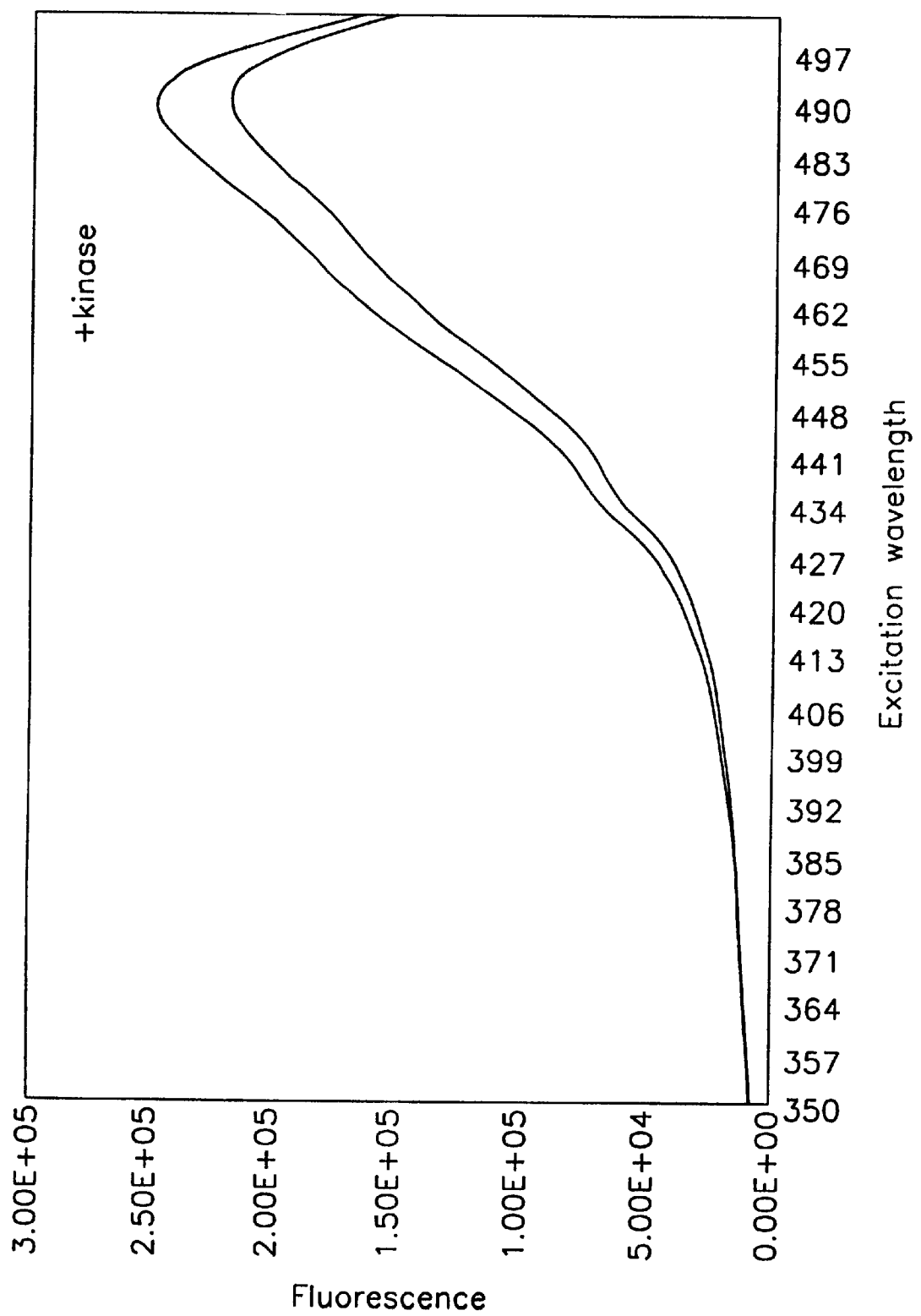

In one embodiment, shown in FIG. 2, a cell is transiently or stably transfected with an expression vector 200 encoding a fluorescent protein substrate containing a phosphorylation site for the enzyme to be assayed. This expression vector optionally includes controlling nucleotide sequences such as promotor or enhancing elements. The expression vector expresses the fluorescent protein substrate 210 that contains the phosphorylation site 211 for the kinase to be detected. The enzyme to be assayed may either be intrinsic to the cell or may be introduced by stable transfection or transient co-transfection with another expression vector encoding the enzyme and optionally including controlling nucleotide sequences such as promoter or enhancer elements. The fluorescent protein substrate and the enzyme preferably are located in the same cellular compartment so that they have more opportunity to come into contact.

If the cell possesses a high degree of enzyme activity (K="kinase" 220), the fluorescent protein substrate will be phosphorylated 230 ($PO_4$), usually through the hydrolysis of ATP. If the cell does not possess kinase activity, or possesses very little, the cell contains substantial amounts of un-phosphorylated substrate 240. Upon excitation with light of the appropriate wavelength ($hv_1$) the phosphorylated substrate will fluoresce light ($hv_2$). Un-phosphorylated substrate exhibits different fluorescent characteristics upon excitation at the same wavelength, and may, for example, not fluoresce at all, or fluoresce weakly. The amount of the fluorescent property is measured generally using the optics 250 and detector 260 of a fluorimeter.

If the cell contains phosphatases that compete with the protein kinases, removing the phosphate from the protein substrate, the level of enzyme activity in the cell can reach an equilibrium between phosphorylated and un-phosphorylated states of the protein substrate, and the fluorescence characteristics will reflect this equilibrium level. In one aspect, this method can be used to compare mutant cells to identify which ones possess greater or lesser ratio of kinase to phosphatase activity. Such cells can be sorted by a fluorescent cell sorter based on fluorescence.

A contemplated variation of the above assay is to use the controlling nucleotide sequences to produce a sudden increase in the expression of either the fluorescent protein substrate or the enzyme being assayed, e.g., by inducing expression of the construct. A fluorescent property is monitored at one or more time intervals after the onset of increased expression. A high amount of the property associated with phosphorylated state reflects a large amount or high efficiency of the kinase. This kinetic determination has the advantage of minimizing any dependency of the assay on the rates of degradation or loss of the fluorescent protein moieties.

In another embodiment, the vector may be incorporated into an entire organism by standard transgenic or gene replacement techniques. An expression vector capable of expressing the enzyme optionally may be incorporated into the entire organism by standard transgenic or gene replacement techniques. Then, a sample from the organism containing the protein substrate is tested. For example, cell or tissue homogenates, individual cells, or samples of body fluids, such as blood, can be tested.

II. SCREENING ASSAYS

The enzymatic assays of the invention can be used in drug screening assays to determine whether a compound alters the activity of a protein kinase. In one embodiment, the assay is performed on a sample in vitro containing the enzyme. A sample containing a known amount of enzyme activity is mixed with a substrate of the invention and with a test compound. The amount of the enzyme activity in the sample is then determined as above, e.g., by measuring the amount of a fluorescent property at a first and second time after contact between the sample, the protein substrate, a phosphate substrate, and the compound. Then the amount of activity per mole of enzyme in the presence of the test compound is compared with the activity per mole of enzyme in the absence of the test compound. A difference indicates that the test compound alters the activity of the enzyme.

In another embodiment, the ability of a compound to alter kinase activity in vivo is determined. In an in vivo assay, cells transfected with a expression vector encoding a substrate of the invention are exposed to different amounts of the test compound, and the effect on fluorescence in each cell can be determined. Typically, the difference is calibrated against standard measurements to yield an absolute amount of kinase activity. A test compound that inhibits or blocks the activity or expression of the kinase can be detected by a relative increase in the property associated with the unphosphorylated state. The cell can also be transfected with an expression vector to co-express the kinase or an upstream signaling component such as a receptor, and fluorescent substrate. This method is useful for detecting signaling to a protein kinase of interest from an upstream component of the signaling pathway. If a signal from an upstream molecule, e.g., a receptor, is inhibited by a drug activity, then the kinase activity will not be altered from basal. This provides a method for screening for compounds which affect cellular events (including receptor-ligand binding, protein-protein interactions or kinase activation) which signal to the target kinase.

This invention also provides kits containing the fluorescent protein substrate and a phosphate substrate for the protein kinase. In one embodiment, the kit has a container holding the fluorescent protein substrate and another container holding the phosphate substrate. Protein kinases of known activity could be included for use as positive controls and standards.

III. FLUORESCENT PROTEIN SUBSTRATES FOR PROTEIN KINASES

As used herein, the term "fluorescent property" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy. A measurable difference in any one of these properties between the phosphorylated and unphosphorylated states suffices for the utility of the fluorescent protein substrates of the invention in assays for kinase activity. A measurable difference can be determined by determining the amount of any quantitative fluorescent property, e.g., the amount of fluorescence at a particular wavelength, or the integral of fluorescence over the emission spectrum. Optimally, the protein substrates are selected to have fluorescent properties that are easily distinguishable in the un-phosphorylated and phosphorylated states. Determining ratios of excitation amplitude or emission amplitude at two different wavelengths ("excitation amplitude ratioing" and "emission amplitude ratioing", respectively) are particularly advantageous because the ratioing process provides an internal reference and cancels out variations in the absolute brightness of the excitation source, the sensitivity of the detector, and light scattering or quenching by the sample. Furthermore, if phosphorylation of the protein substrate changes its ratio of excitation or emission amplitudes at two different wavelengths, then such ratios measure the extent of phosphorylation independent of the absolute quantity of the protein substrate. Some of the fluorescent protein substrates described herein do exhibit a phosphorylation-induced change in the ratio of excitation amplitudes at two different wavelengths. Even if a fluorescent protein substrate does not exhibit a phosphorylation-induced change in excitation or emission amplitudes at two wavelengths, cells can be provided that co-express another fluorescent protein that is not sensitive to phosphorylation and whose excitation or emission spectrum is peaked at wavelengths distinct from those of the phosphorylation substrate. Provided that the expression of the two proteins are both controlled by the same nucleotide control sequences, their expression levels should be closely linked. Therefore ratioing the excitation or emission amplitude of the phosphorylation substrate at its preferred wavelength to the corresponding excitation or emission amplitude of the phosphorylation-insensitive reference protein at its separate preferred wavelength is an alternative method for canceling out variations in the absolute quantity of cells or overall level of protein expression.

A. Fluorescent Proteins

As used herein, the term "fluorescent protein" refers to any protein capable of fluorescence when excited with appropriate electromagnetic radiation. This includes fluorescent proteins whose amino acid sequences are either naturally occurring or engineered (i.e., analogs). Many cnidarians use green fluorescent proteins ("GFPs") as energy-transfer acceptors in bioluminescence. A "green fluorescent protein," as used herein, is a protein that fluoresces green light. Similarly, "blue fluorescent proteins" fluoresce blue light and "red fluorescent proteins" fluoresce red light. GFPs have been isolated from the Pacific Northwest jellyfish, *Aequorea Victoria,* the sea pansy, *Renilla reniformis,* and *Phialidium gregarium.* W. W. Ward et al., *Photochem. Photobiol.,* 35:803–808 (1982); L. D. Levine et al., *Comp. Biochem. Physiol.,* 72B:77–85 (1982).

A variety of Aequorea-related fluorescent proteins having useful excitation and emission spectra have been engineered by modifying the amino acid sequence of a naturally occurring GFP from *Aequorea victoria.* (D.C. Prasher et al., *Gene,* 111:229–233 (1992); R. Heim et al., *Proc. Natl. Acad. Sci., USA,* 91:12501–04 (1994); U.S. patent application Ser. No. 08/337,915, filed Nov. 10, 1994; International application PCT/US95/14692, filed Nov. 10, 1995.)

As used herein, a fluorescent protein is an "Aequorea-related fluorescent protein" if any contiguous sequence of 150 amino acids of the fluorescent protein has at least 85% sequence identity with an amino acid sequence, either contiguous or non-contiguous, from the 238 amino-acid wild-type Aequorea green fluorescent protein of FIG. 3 (SEQ ID NO:2). More preferably, a fluorescent protein is an Aequorea-related fluorescent protein if any contiguous sequence of 200 amino acids of the fluorescent protein has at least 95% sequence identity with an amino acid sequence, either contiguous or non-contiguous, from the wild type Aequorea green fluorescent protein of FIG. 3 (SEQ ID NO:2). Similarly, the fluorescent protein may be related to Renilla or Phialidium wild-type fluorescent proteins using the same standards.

Optimal alignment of sequences for aligning a comparison window may be conducted by the local homology algorithm of Smith and Waterman (1981) *Adv. Appl. Math.,* 2:482, by the homology alignment algorithm of Needleman and Wunsch (1970) *J. Mol. Biol.,* 48:443, by the search for similarity method of Pearson and Lipman (1988) *Proc. Natl. Acad. Sci., U.S.A.,* 85:2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection. The best alignment (i.e., resulting in the highest percentage of homology over the comparison window, i.e., 150 or 200 amino acids) generated by the various methods is selected.

The percentage of sequence identity is calculated by comparing two optimally aligned sequences over the window of comparison, determining the number of positions at which the identical amino acid occurs in both sequences to yield the number of matched positions, dividing the number of matched positions by the total number of positions in the window of comparison (i.e., the window size), and multiplying the result by 100 to yield the percentage of sequence identity.

Aequorea-related fluorescent proteins include, for example and without limitation, wild-type (native) *Aequorea victoria* GFP (D. C. Prasher et al., "Primary structure of the Aequorea Victoria green fluorescent protein," *Gene,* (1992) 111:229–33), whose nucleotide sequence (SEQ ID NO: 1) and deduced amino acid sequence (SEQ ID NO:2) are presented in FIG. 3, allelic variants of this sequence, e.g., Q80R, which has the glutamine residue at position 80 substituted with arginine (M. Chalfie et al., *Science,* (1994) 263:802–805), those Aequorea-related engineered versions described in Table I, variants that include one or more folding mutations and fragments of these proteins that are fluorescent, such as Aequorea green fluorescent protein from which the two amino-terminal amino acids have been removed. Several of these contain different aromatic amino acids within the central chromophore and fluoresce at a distinctly shorter wavelength than wild type species. For example, mutants P4 and P4-3 contain (in addition to other mutations) the substitution Y66H, whereas W2 and W7 contain (in addition to other mutations) Y66W. Other mutations both close to the chromophore region of the protein and remote from it in primary sequence may affect the spectral properties of GFP and are listed in the first part of the table below.

TABLE I

| Clone | Mutation(s) | Excitation max (nm) | Emission max (nm) | Extinct. Coeff. ($M^{-1}cm^{-1}$) | Quantum yield |
|---|---|---|---|---|---|
| Wild type | none | 395 (475) | 508 | 21,000 (7,150) | 0.77 |
| P4 | Y66H | 383 | 447 | 13,500 | 0.21 |
| P4-3 | Y66H Y145F | 381 | 445 | 14,000 | 0.38 |
| W7 | Y66W N146I M153T V163A N212K | 433 (453) | 475 (501) | 18,000 (17,100) | 0.67 |
| W2 | Y66W I123V Y145H H148R M153T V163A N212K | 432 (453) | 480 | 10,000 (9,600) | 0.72 |
| S65T | S65T | 489 | 511 | 39,200 | 0.68 |
| P4-1 | S65T M153A K238E | 504 (396) | 514 | 14,500 (8,600) | 0.53 |
| S65A | S65A | 471 | 504 | | |
| S65C | S65C | 479 | 507 | | |
| S65L | S65L | 484 | 510 | | |
| Y66F | Y66F | 360 | 442 | | |
| Y66W | Y66W | 458 | 480 | | |

Additional mutations in Aequorea-related fluorescent proteins, referred to as "folding mutations," improve the ability of GFP to fold at higher temperatures, and to be more fluorescent when expressed in mammalian cells, but have little or no effect on the peak wavelengths of excitation and emission. It should be noted that these may be combined with mutations that influence the spectral properties of GFP to produce proteins with altered spectral and folding properties. Folding mutations include: T44A, F64L, V68L, S72A, F99S, Y145F, N146I, M153T or A, V163A, I167T, S175G, S205T and N212K.

This invention contemplates the use of other fluorescent proteins in fluorescent protein substrates for protein kinases. The cloning and expression of yellow fluorescent protein from Vibrio fischeri strain Y-1 has been described by T. O. Baldwin et al., *Biochemistry* (1990) 29:5509–15. This protein requires flavins as fluorescent co-factors. The cloning of Peridinin-chlorophyll a binding protein from the dinoflagellate Symbiodinium sp. was described by B. J. Morris et al., *Plant Molecular Biology*, (1994) 24:673:77. One useful aspect of this protein is that it fluoresces red. The cloning of phycobiliproteins from marine cyanobacteria such as Synechococcus, e.g., phycoerythrin and phycocyanin, is described in S. M. Wilbanks et al., *J. Biol. Chem.* (1993) 268:1226–35. These proteins require phycobilins as fluorescent co-factors, whose insertion into the proteins involves auxiliary enzymes. The proteins fluoresce at yellow to red wavelengths.

As used herein, the "fluorescent protein moiety" of a fluorescent protein substrate is that portion of the amino acid sequence of a fluorescent protein substrate which, when the amino acid sequence of the fluorescent protein substrate is optimally aligned with the amino acid sequence of a naturally occurring fluorescent protein, lies between the amino terminal and carboxy terminal amino acids, inclusive, of the amino acid sequence of the naturally occurring fluorescent protein.

It has been found that fluorescent proteins can be genetically fused to other target proteins and used as markers to identify the location and amount of the target protein produced. Accordingly, this invention provides fusion proteins comprising a fluorescent protein moiety and additional amino acid sequences. Such sequences can be, for example, up to about 15, up to about 50, up to about 150 or up to about 1000 amino acids long. The fusion proteins possess the ability to fluoresce when excited by electromagnetic radiation. In one embodiment, the fusion protein comprises a polyhistidine tag to aid in purification of the protein.

B. Phosphorylation Sites For Protein Kinases

Fluorescent protein substrates for a protein kinase are the subset of fluorescent proteins as defined above whose amino acid sequence includes a phosphorylation site. Fluorescent protein substrates can be made by modifying the amino acid sequence of an existing fluorescent protein to include a phosphorylation site for a protein kinase. Fluorescent protein substrates for protein kinases are not meant to include naturally occurring fluorescent proteins or currently known mutant fluorescent proteins. Such previously known fluorescent proteins or mutants may be substrates for protein kinases, but do not exhibit any detectable change in fluorescent properties upon phosphorylation.

As used herein, the term "phosphorylation site for a protein kinase" refers to an amino acid sequence which, as part of a polypeptide, is recognized by a protein kinase for the attachment of a phosphate moiety. The phosphorylation site can be a site recognized by, for example, protein kinase A, a cGMP-dependent protein kinase, protein kinase C, $Ca^{2+}$/calmodulin-dependent protein kinase I, $Ca^{2+}$/calmodulin-dependent protein kinase II or MAP kinase activated protein kinase type 1.

The preferred consensus sequence for protein kinase A is RRXSZ (SEQ ID NO:3) or RRXTZ (SEQ ID NO:4), wherein X is any amino acid and Z is a hydrophobic amino acid, preferably valine, leucine or isoleucine. Many variations in the above sequence are allowed, but generally exhibit poorer kinetics. For example, lysine (K) can be substituted for the second arginine. Many consensus sequences for other protein kinases have been tabulated, e.g. by Kemp, B. E. and Pearson, R. B. (1990) *Trends Biochem. Sci.* 15: 342–346; Songyang, Z. et al. (1994) *Current Biology* 4: 973–982.

For example, a fluorescent protein substrate selective for phosphorylation by cGMP-dependent protein kinase can include the following consensus sequence: BKISASEFDR PLR (SEQ ID NO:5), where B represents either lysine (K) or arginine (R), and the first S is the site of phosphorylation (Colbran et al. (1992) *J. Biol. Chem.* 267: 9589–9594). The residues DRPLR (SEQ ID NO:6) are less critical than the phenylalanine (F) just preceding them for specific recognition by cGMP-dependent protein kinase in preference to cAMP-dependent protein kinase.

Either synthetic or naturally occurring motifs can be used to create a protein kinase phosphorylation site. For example, peptides including the motif XRXXSXRX (SEQ ID NO:7), wherein X is any amino acid, are among the best synthetic substrates (Kemp and Pearson, supra) for protein kinase C. Alternatively, the Myristoylated Alanine-Rich Kinase C substrate ("MARCKS") is one of the best substrates for PKC and is a real target for the kinase in vivo. The sequence around the phosphorylation site of MARCKS is KKKKRF-SFK (SEQ ID NO:8) (Graff et al. (1991) *J. Biol. Chem.* 266:14390–14398). Either of these two sequences can be incorporated into a fluorescent protein to make it a substrate for protein kinase C.

A protein substrate for $Ca^{2+}$/calmodulin-dependent protein kinase I is derived from the sequence of synapsin I, a known optimal substrate for this kinase. The recognition sequence around the phosphorylation site is LRRLSDSNF (SEQ ID NO:9) (Lee et al. (1994) *Proc. Natl. Acad. Sci. USA* 91:6413–6417).

A protein substrate selective for $Ca^{2+}$/calmodulin-dependent protein kinase II is derived from the sequence of glycogen synthase, a known optimal substrate for this kinase. The recognition sequence around the phosphorylation site is KKLNRTLTVA (SEQ ID NO: 10) (Stokoe et al. (1993) *Biochem. J.* 296:843–849). A small change in this sequence to KKANRTLSVA (SEQ ID NO: 11) makes the latter specific for MAP kinase activated protein kinase type 1.

In one embodiment, the fluorescent protein substrate contains a phosphorylation site around one of the termini, in particular, the amino-terminus, of the fluorescent protein moiety. The site preferably is located in a position within five, ten, fifteen, or twenty amino acids of a position corresponding to the wild type amino-terminal amino acid of the fluorescent protein moiety ("within twenty amino acids of the amino-terminus"). This includes sites engineered into the existing amino acid sequence of the fluorescent protein moiety and sites produces by extending the amino terminus of the fluorescent protein moiety.

One may, for example, modify the existing sequence of wild type Aequorea GFP or a variant or it as listed above to include a phosphorylation site within the first ten or twenty amino acids. In one embodiment, the naturally occurring sequence is modified as follows:

wild type: MSKGEELFTG (SEQ ID NO:43)

substrate: MRRRRSIITG (SEQ ID NO: 12).

One may include modifying the naturally occurring sequence of Aequorea GFP by introducing a phosphorylation site into an extended amino acid sequence of such a protein created by adding flanking sequences to the amino terminus, for example:

wild type: MSKGEELFTG (SEQ ID NO:43)

substrate: MRRRRSIIIIFTG (SEQ ID NO: 13).

Fluorescent protein substrates having a phosphorylation site around a terminus of the fluorescent protein moiety offer the following advantages. First, it is often desirable to append additional amino acid residues onto the fluorescent protein moiety in order to create a specific phosphorylation consensus sequence. Such a sequence is much less likely to disrupt the folding pattern of the fluorescent protein when appended onto the terminus than when inserted into the interior of the protein sequence. Second, different phosphorylation motifs can be interchanged without significant disruption of GFP therefore providing a general method of measuring different kinases. Third, the phosphorylation site is exposed to the surface of the protein and, therefore, more accessible to protein kinases. Fourth, we have discovered that phosphorylation at sites close to the N-terminus of GFP can provide large changes in fluorescent properties if the site of phosphorylation is chosen such that the Ser or Thr residue which is phosphorylated occupies a position which in the wild-type protein was originally negatively or positively charged. Specifically, replacement of Glu 6 by a non-charged Ser or Thr residue can significantly disrupt fluorescence of GFP when made within the right context of surrounding amino acids. Phosphorylation of the serine or threonine will restore negative charge to this position and thereby increases fluorescence.

In another embodiment, the fluorescent protein substrate includes a phosphorylation site remote from the terminus, e.g., that is separated by more than about twenty amino acids from the terminus of the fluorescent protein moiety and within the fluorescent protein moiety. One embodiment of this form includes the Aequorea-related fluorescent protein substrate comprising the substitution H217S, creating a consensus protein kinase A phosphorylation site. Additionally, phosphorylation sites comprising the following alterations based on the sequence of wild type Aequorea GFP exhibit fluorescent changes upon phosphorylation: 69RRFSA (SEQ ID NO: 14) and 214KRDSM (SEQ ID NO: 15).

The practitioner should consider the following in selecting amino acids for substitution within the fluorescent protein moiety remote in primary amino acid sequence from the terminus. First, it is preferable to select amino acid sequences within the fluorescent protein moiety that resemble the sequence of the phosphorylation site. In this way, fewer amino acid substitutions in the native protein are needed to introduce the phosphorylation site into the fluorescent protein. For example, protein kinase A recognizes the sequence RRXSZ (SEQ ID NO:46) or RRXTZ (SEQ ID NO:47), wherein X is any amino acid and Z is a hydrophobic amino acid. Serine or threonine is the site of phosphorylation. It is preferable to introduce this sequence into the fluorescent protein moiety at sequences already containing Ser or Thr, so that Ser or Thr are not substituted in the protein. More preferably the phosphorylation site is created at locations having some existing homology to the sequence recognized by protein kinase A, e.g., having a proximal Arg or hydrophobic residues with the same spatial relationship as in the phosphorylation site.

Second, locations on the surface of the fluorescent protein are preferred for phosphorylation sites. This is because surface locations are more likely to be accessible to protein kinases than interior locations. Surface locations can be identified by computer modeling of the fluorescent protein structure or by reference to the crystal structure of Aequorea GFP. Also, charged amino acids in the fluorescent protein are more likely to lie on the surface than inside the fluorescent protein, because such amino acids are more likely to be exposed to water in the environment.

In cases where the phosphorylation site is either at the N-terminus or remote from it, the amino acid context around the phosphorylation site needs to be optimized in order to maximize the change in fluorescence. Amino acid substitutions that change large bulky and or hydrophobic amino acids to smaller and less hydrophobic replacements are generally helpful. Similarly large charged amino acids can be replaced by smaller, less charged amino acids. For example:

a/Hydrophobic to less hydrophobic

Phe to Leu

Leu to Ala b/ Charged to charged but smaller
Glu to Asp
Arg to Lys
c/ Charged to less charged
Glu to Gln
Asp to Asn
d/ Charged to polar
Glu to Thr
Asp to Ser
e/ Charged to non-polar
Glu to Leu
Asp to Ala These changes can be accomplished by directed means or using random iterative approaches where changes are made randomly and the best ones selected based upon their change in fluorescent properties after phosphorylation by an appropriate kinase.

Third, amino acids at distant locations from the actual site of phosphorylation can be varied to enhance fluorescence changes upon phosphorylation. These mutations can be created through site directed mutagenesis, or through random mutagenesis, for example by error-prone PCR, to identify mutations that enhance either absolute fluorescence or the change in fluorescence upon phosphorylation. The identification of mutants remote in primary sequence from the N-terminus identifies potentially interacting sequences which may provide additional areas in which further mutagenesis could be used to refine the change in fluorescence upon phosphorylation. For example, it has been determined that mutations around the amino terminus phosphorylation site interact (either transiently during folding, or in a stable fashion) with amino acids at positions 171 and 172, and that point mutations that significantly disrupt fluorescence of GFP by changing negative to positive charges near the amino terminus can be rescued by changing a positive to a negative charge at position 171.

In the phosphorylation mutant 50 the sequence is a/ and for reference the wild type sequence b/ is listed below.

a/ MSKRRDSLT (SEQ ID NO: 16)
b/ MSKGEELFT (SEQ ID NO:44)

The phosphorylation mutant has only 7% of the fluorescence of wild type protein. However, its fluorescence can be restored to 80% of wild type by 2 amino acid changes, E171K and I172V, positions which are quite remote in linear sequence from the amino terminus.

Thus, changes in charge at E171K (negative to positive) can almost completely restore the fluorescence of the phosphorylation mutant, strongly suggesting that the original loss of fluorescence arose primarily through changes in charge caused by the point mutations. It is clear that the addition and loss of charge at positions around, and at the phosphorylation site, have a significant impact on fluorescence formation. The fact that charge alone can significantly affect the fluorescence properties of GFP is highly significant within the scope of the present application since phosphorylation involves the addition of 2 negative charges associated with the phosphate group ($OPO_3^{-2}$) on the serine residue.

In the above case the mutations restore fluorescence of the phosphorylation mutant, without significantly increasing the magnitude of the change in fluorescence upon phosphorylation. Nevertheless the identification of these positions in GFP provides a valuable tool to further optimize changes in fluorescence upon phosphorylation by creating random mutations at codons around positions 171, 172 and 173 to identify mutations that enhance changes in fluorescence upon phosphorylation.

This can be achieved by co-expressing the kinase of interest with the fluorescent substrate of the invention containing random mutations which may enhance the fluorescence changes upon phosphorylation in bacteria (in the example above these would be NNK mutations at codons 171, 172 and 173, where N represents a random choice of any of the four bases and K represents a random choice of guanine or thymine). The expression vector containing the mutated fluorescent substrates and the kinase are transformed into host bacteria and the individual bacterial colonies grown up. Each colony is derived from a single cell, and hence contains a single unique mutant fluorescent substrate grown up.

The individual colonies may then be grown up and screened for fluorescence either by fluorescence activated cell sorting (FACS), or by observation under a microscope. Those that exhibit the greatest fluorescence can then be rescreened under conditions in which the kinase gene is inactivated. This can be achieved by appropriate digests of the kinase gene by restriction enzymes that specifically cut within the kinase but not GFP. Comparison of the brightness of the mutant first in the presence of kinase then in its absence indicates the relative effect of phosphorylation on the mutant GFP.

C. Production Of Fluorescent Protein Substrates For Protein Kinases

While certain fluorescent protein substrates for protein kinases can be prepared chemically, for example, by coupling a peptide moiety to the amino terminus of a fluorescent protein, it is preferable produce fluorescent protein substrates recombinantly.

Recombinant production of a fluorescent protein substrate involves expressing a nucleic acid molecule having sequences that encode the protein. As used herein, the term "nucleic acid molecule" includes both DNA and RNA molecules. It will be understood that when a nucleic acid molecule is said to have a DNA sequence, this also includes RNA molecules having the corresponding RNA sequence in which "U" replaces "T." The term "recombinant nucleic acid molecule" refers to a nucleic acid molecule which is not naturally occurring, and which comprises two nucleotide sequences which are not naturally joined together. Recombinant nucleic acid molecules are produced by artificial combination, e.g., genetic engineering techniques or chemical synthesis.

In one embodiment, the nucleic acid encodes a fusion protein in which a single polypeptide includes the fluorescent protein moiety within a longer polypeptide. In another embodiment the nucleic acid encodes the amino acid sequence of consisting essentially of a fluorescent protein modified to include a phosphorylation site. In either case, nucleic acids that encode fluorescent proteins are useful as starting materials.

Nucleic acids encoding fluorescent proteins can be obtained by methods known in the art. For example, a nucleic acid encoding a green fluorescent protein can be isolated by polymerase chain reaction of cDNA from *A. Victoria* using primers based on the DNA sequence of *A. Victoria* green fluorescent protein, as presented in FIG. 3. PCR methods are described in, for example, U.S. Pat. No. 4,683,195; Mullis et al. (1987) *Cold Spring Harbor Symp. Quant. Biol.* 51:263; and Erlich, ed., *PCR Technology,* (Stockton Press, NY, 1989).

Mutant versions of fluorescent proteins can be made by site-specific mutagenesis of other nucleic acids encoding fluorescent proteins, or by random mutagenesis caused by increasing the error rate of PCR of the original polynucleotide with 0.1 mM MnCl$_2$ and unbalanced nucleotide concentrations. See, e.g., U.S. patent application Ser. No. 08/337,915, filed Nov. 10, 1994 or International application PCT/US95/14692, filed Nov. 10, 1995.

Nucleic acids encoding fluorescent protein substrates which are fusions between a polypeptide including a phosphorylation site and a fluorescent protein and can be made by ligating nucleic acids that encode each of these. Nucleic acids encoding fluorescent protein substrates which include the amino acid sequence of a fluorescent protein in which one or more amino acids in the amino acid sequence of a fluorescent protein are substituted to create a phosphorylation site can be created by, for example, site specific mutagenesis of a nucleic acid encoding a fluorescent protein.

The construction of expression vectors and the expression of genes in transfected cells involves the use of molecular cloning techniques also well known in the art. Sambrook et al., *Molecular Cloning—A Laboratory Manual,* Cold Spring Harbor Laboratory, Cold Spring Harbor, N.Y., (1989) and *Current Protocols in Molecular Biology,* F. M. Ausubel et al., eds., (Current Protocols, a joint venture between Greene Publishing Associates, Inc. and John Wiley & Sons, Inc.

Nucleic acids used to transfect cells with sequences coding for expression of the polypeptide of interest generally will be in the form of an expression vector including expression control sequences operatively linked to a nucleotide sequence coding for expression of the polypeptide. As used, the term nucleotide sequence "coding for expression of" a polypeptide refers to a sequence that, upon transcription and translation of mRNA, produces the polypeptide. As any person skilled in the art recognizes, this includes all degenerate nucleic acid sequences encoding the same amino acid sequence. This can include sequences containing, e.g., introns. As used herein, the term "expression control sequences" refers to nucleic acid sequences that regulate the expression of a nucleic acid sequence to which it is operatively linked. Expression control sequences are "operatively linked" to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons.

The recombinant nucleic acid can be incorporated into an expression vector comprising expression control sequences operatively linked to the recombinant nucleic acid. The expression vector can be adapted for function in prokaryotes or eukaryotes by inclusion of appropriate promoters, replication sequences, markers, etc.

The expression vector can be transfected into a host cell for expression of the recombinant nucleic acid. Host cells can be selected for high levels of expression in order to purify the protein. *E. coli* is useful for this purpose. Alternatively, the host cell can be a prokaryotic or eukaryotic cell selected to study the activity of an enzyme produced by the cell. The cell can be, e.g., a cultured cell or a cell in vivo.

Recombinant fluorescent protein substrates can be produced by expression of nucleic acid encoding for the protein in *E. coli.* Aequorea-related fluorescent proteins are best expressed by cells cultured between about 15° C. and 30° C. but higher temperatures (e.g. 37° C.) are possible. After synthesis, these enzymes are stable at higher temperatures (e.g., 37° C.) and can be used in assays at those temperatures.

The construct can also contain a tag to simplify isolation of the substrate. For example, a polyhistidine tag of, e.g., six histidine residues, can be incorporated at the amino or carboxyl terminal of the fluorescent protein substrate. The polyhistidine tag allows convenient isolation of the protein in a single step by nickel-chelate chromatography.

Alternatively, the substrates need not be isolated from the host cells. This method is particularly advantageous for the assaying for the presence of protein kinase activity in situ.

IV. LIBRARIES OF CANDIDATE SUBSTRATES

The inclusion of a phosphorylation site around the amino terminus of a fluorescent protein moiety can provide a fluorescent protein that, when phosphorylated, can alter a fluorescent property of the protein. Accordingly, this invention provides libraries of fluorescent protein candidate substrates useful for screening in the identification and characterization of sequences that can be recognized and efficiently phosphorylated by a kinase. Libraries of these proteins can be screened to identify sequences that can be phosphorylated by kinases of unknown substrate specificity, or to characterize differences in kinase activity in, or from, diseased and normal cells or tissues.

As used herein, a "library" refers to a collection containing at least 10 different members. Each member of a fluorescent protein candidate substrate library comprises a fluorescent protein moiety and a variable peptide moiety, which is preferably located near the amino-terminus of the fluorescent protein moiety and preferably has fewer than about 15 amino acids. The variety of amino acid sequences for the peptide moiety is at the discretion of the practitioner. For example, the library can contain a quite diverse collection of variable peptide moieties in which most or all of the amino acid positions are subjected to a non-zero but low probability of substitution. Also, the library can contain variable peptide moieties having an amino acid sequence in which only a few, e.g., one to ten, amino acid positions are varied, but the probability of substitution at each position is relatively high.

Preferably, libraries of fluorescent protein candidate substrates are created by expressing protein from libraries of recombinant nucleic acid molecules having expression control sequences operatively linked to nucleic acid sequences that code for the expression of different fluorescent protein candidate substrates. Methods of making nucleic acid molecules encoding a diverse collection of peptides are described in, for example, U.S. Pat. No. 5,432,018 (Dower et al.), U.S. Pat. No. 5,223,409 (Ladner et al.), U.S. Pat. No. 5,264,563 (Huse), and International patent publication WO 92/06176 (Huse et al.). For expression of fluorescent protein candidate substrates, recombinant nucleic acid molecules are used to transfect cells, such that each cell contains a member of the library. This produces, in turn, a library of host cells capable of expressing the library of different fluorescent protein candidate substrates. The library of host cells is useful in the screening methods of this invention.

In one method of creating such a library, a diverse collection of oligonucleotides having preferably random codon sequences are combined to create polynucleotides encoding peptides having a desired number of amino acids. The oligonucleotides preferably are prepared by chemical synthesis. The polynucleotides encoding variable peptide moiety can then be coupled to the 5' end of a nucleic acid coding for the expression of a fluorescent protein moiety or a carboxy-terminal portion of it. That is, the fluorescent protein moiety can be cut back to eliminate up to 20 amino acids of the reference fluorescent protein. This creates a recombinant nucleic acid molecule coding for the expression of a fluorescent protein candidate substrate having a peptide moiety fused to the amino terminus of the fluorescent protein. This recombinant nucleic acid molecule is then inserted into an expression vector to create a recombinant nucleic acid molecule comprising expression control sequences operatively linked to the sequences encoding the candidate substrate.

To generate the collection of oligonucleotides which forms a series of codons encoding a random collection of amino acids and which is ultimately cloned into the vector, a codon motif is used, such as $(NNK)_x$, where N may be A, C, G, or T (nominally equimolar), K is G or T (nominally equimolar), and x is the desired number of amino acids in the peptide moiety, e.g., 15 to produce a library of 15-mer peptides. The third position may also be G or C, designated "S". Thus, NNK or NNS (i) code for all the amino acids, (ii) code for only one stop codon, and (iii) reduce the range of codon bias from 6:1 to 3:1. The expression of peptides from randomly generated mixtures of oligonucleotides in appropriate recombinant vectors is discussed in Oliphant et al., Gene 44:177–183 (1986).

An exemplified codon motif $(NNK)_6$ (SEQ ID NO: 17) produces 32 codons, one for each of 12 amino acids, two for each of five amino acids, three for each of three amino acids and one (amber) stop codon. Although this motif produces a codon distribution as equitable as available with standard methods of oligonucleotide synthesis, it results in a bias against peptides containing one-codon residues.

An alternative approach to minimize the bias against one-codon residues involves the synthesis of 20 activated tri-nucleotides, each representing the codon for one of the 20 genetically encoded amino acids. These are synthesized by conventional means, removed from the support but maintaining the base and 5-HO-protecting groups, and activating by the addition of 3'O-phosphoramidite (and phosphate protection with beta-cyanoethyl groups) by the method used for the activation of mononucleosides, as generally described in McBride and Caruthers, Tetrahedron Letters 22:245 (1983). Degenerate "oligocodons" are prepared using these trimers as building blocks. The trimers are mixed at the desired molar ratios and installed in the synthesizer. The ratios will usually be approximately equimolar, but may be a controlled unequal ratio to obtain the over- to under-representation of certain amino acids coded for by the degenerate oligonucleotide collection. The condensation of the trimers to form the oligocodons is done essentially as described for conventional synthesis employing activated mononucleosides as building blocks. See generally, Atkinson and Smith, Oligonucleotide Synthesis, M. J. Gait, ed. p35–82 (1984). Thus, this procedure generates a population of oligonucleotides for cloning that is capable of encoding an equal distribution (or a controlled unequal distribution) of the possible peptide sequences.

Libraries of amino terminal phosphorylation sites may also be annealed to libraries of randomly mutated GFP sequences to enable the selection of optimally responding substrates.

V. METHODS FOR SCREENING LIBRARIES OF CANDIDATE SUBSTRATES

Libraries of host cells expressing fluorescent protein candidate substrates are useful in identifying fluorescent proteins having peptide moieties that alter a fluorescent property of the fluorescent protein. Several methods of using the libraries are envisioned. In general, one begins with a library of recombinant host cells, each of which expresses a different fluorescent protein candidate substrate. Each cell is expanded into a clonal population that is genetically homogeneous.

In a first method, the desired fluorescent property is measured from each clonal population before and at least one specified time after a known change in intracellular protein kinase activity. This change in kinase activity could be produced by transfection with a gene encoding the kinase, by induction of kinase gene expression using expression control elements, or by any condition that post-translationally modulates activity of a kinase that has already been expressed. Examples of the latter include cell surface receptor mediated elevation of intracellular cAMP to activate cAMP-dependent surface receptor mediated increases of intracellular cGMP to activate cGMP-dependent protein kinase, cytosolic free calcium to activate $Ca^{2+}$/calmodulin-dependent protein kinase types I, II, or IV, or the production of diacylglycerol to activate protein kinase C, etc. One then selects for the clone(s) that show the biggest or fastest change in the desired fluorescence property. This method detects fluorescent protein mutants whose folding and maturation was influenced by phosphorylation as well as those affected by phosphorylation after maturation.

One embodiment of this method exploits the fact that the catalytic subunit of cAMP-dependent protein kinase is constitutively active in the absence of the regulatory subunit and is growth-inhibitory in E. coli and most mammalian cells. Therefore, the cells tend to shed the kinase gene by recombination. The change in kinase activity is obtained by culturing the cells for a time sufficient to lose the kinase gene.

In a second method the host cells do not express the protein kinase of interest. Each clonal population is separately lysed. ATP is then added to the lysate. After an incubation period to allow phosphorylation by background kinases, the fluorescence property is measured. Then exogenous protein kinase is added to the lysate and the fluorescent property is re-measured at one or more specified time points. Again one selects for the clone(s) that show the biggest or fastest change(s) in the desired fluorescence property. Because little or no fresh protein synthesis is likely to occur in the lysate, this method would discriminate against mutants which are sensitive to phosphorylation only during their folding and maturation.

In one embodiment of this method, the lysate is split into two aliquots, one of which is mixed with kinase and ATP, the other of which receives only ATP. One selects for the clone(s) that show the biggest difference in fluorescence property between the two aliquots.

The nucleic acids from cells exhibiting the different properties can be isolated from the cells. Candidate substrates having different fluorescent properties can be tested further to identify the source of the difference.

The host cell also can be transfected with an expression vector capable of expressing an enzyme, such as a protein kinase, whose effect on the fluorescent property is to be tested.

VI. EXAMPLES

A. Phosphorylation sites located in the amino acid sequence of Aeguorea GFP remote in the primary amino acid sequence from the N-terminus Potential sites for phosphorylation were chosen at or close to positions in GFP which had previously been identified to exert significant effects on fluorescence, or which had a higher probability of surface exposure based on computer algorithms (FIG. 4). For example, in a mutant called H9, Ser202 and Thr203 are mutated to F and I respectively, creating a large change in spectral properties (see also Ehrig et al, 1995). Therefore in one mutant, 199RRLSI (SEQ ID NO: 18), a potential site of phosphorylation was created around Ser202, whose phosphorylation should significantly affect the fluorescent properties. Similarly the amino acids located at positions 72 and 175 have been implicated in increased folding efficiency of GFP at higher temperatures and were made into potential sites of phosphorylation in separate mutants.

A complete list of the positions and amino acid changes made for each phosphorylation mutant in this series is outlined in FIG. 4. GFP was expressed in *E. coli* using the expression plasmid pRSET (Invitrogen), in which the region encoding GFP was fused in frame with nucleotides encoding an N-terminal polyhistidine tag (FIG. 5). The sequence changes were introduced by site-directed mutagenesis using the Bio-Rad mutagenesis kit (Kunkel, T. A. (1985) *Proc. Natl. Acad. Sci.* 82:488–492, Kunkel, T. A., Roberts, J. D., and Zakour, R. A. (1987) *Meth Enzymol* 154:367–382) and confirmed by sequencing. The recombinant proteins were induced with IPTG and expressed in bacteria and purified by nickel affinity chromatography. The sequence changes, relative fluorescence, relative rate of phosphorylation and % change in fluorescence upon phosphorylation are listed in Table II. In those cases where the protein exhibited no fluorescence after insertion of the phosphorylation site no determinations were made on the effect of phosphorylation on fluorescence.

with excess protein kinase A catalytic subunit for 1 hour at 30° C. using the same phosphorylation conditions as described above except that no $^{32}$P-labeled ATP was present and that after the reaction time was complete samples were analyzed in the fluorimeter rather than blotted onto phosphocellulose paper.

The greatest changes in fluorescence occurred in mutant 214KRDSM (SEQ ID NO: 15) which exhibited a 40% change in fluorescence upon phosphorylation. However analysis of the kinetics of phosphorylation using γ-$^{32}$P-labeled ATP demonstrated that the site is poorly phosphorylated by protein kinase A. Wild type GFP contains a mediocre consensus phosphorylation site (25HKFSV, (SEQ ID NO: 45) that can be phosphorylated by protein kinase A in vitro with relatively slow kinetics. While phosphorylation at this position has no detectable effect on the fluorescence of GFP, the rate of phosphorylation at this position is used as an internal control between experiments to determine the relative rates of phosphorylation at sites engineered into the protein by site directed mutagenesis.

B. Phosphorylation sites around the amino terminus

Sites at the N-terminus of GFP were engineered into GFP by PCR. Initial studies attempted to preserve the native sequence as much as possible. As discussed earlier the positions chosen for phosphorylation were within the first 5 amino acids of GFP and encompassed all charged residues within this region. The sequence changes, relative fluorescence, relative rates of phosphorylation and % change in fluorescence upon phosphorylation are tabulated in Table III.

TABLE II

Relative fluorescence, rate of phosphorylation and change in fluorescence upon phosphorylation for mutants incorporating phosphorylation sites remote from the N-terminus

| SEQ ID NO: | Sequence | Fluorescence before phosphorylation (% of wild type) | Relative rates of phosphorylation | % Change in fluorescence after incubation with kinase |
|---|---|---|---|---|
| 19 | 25RRFSV | 95 | 1.75 | −5 |
| 20 | 68RRFSR | 0 | n.d | n.d |
| 14 | 68RRFSA | 6 | 0.6 | +10 |
| 21 | 94RRSIF | 0 | n.d | n.d |
| 22 | 131RRGSIL | 0 | n.d | n.d |
| 23 | 155KRKSGI | 86 | 2.5 | 0 |
| 24 | 172RRGSV | 90 | 1.57 | 0 |
| 18 | 199RRLSI | 0 | n.d | n.d |
| 15 | 214KRDSM | 21 | 1.88 | +40 |

Bold letters indicate site of phosphorylation. Numbers prior to the sequence indicate amino acid position in wild type GFP (FIG. 3, SEQ ID NO:2) where phosphorylation site starts. The relative rates of phosphorylation compare the rate of phosphorylation of the given phosphorylation site with the endogenous protein kinase A phosphorylation site in Aequorea GFP (HKFSV SEQ ID NO: 45) measured by incorporation of $^{32}$P after incubation of the purified substrate and protein kinase A catalytic subunit in the presence of $^{32}$P-labelled ATP using 3 μg GFP, 5 μg protein kinase A catalytic subunit for 10 minutes at 30° C. in standard phosphorylation buffer (20 mM MOPS pH 6.5, 100 mM KCI, 100 μM ATP, 3 mM MgCl$_2$ 1 mM DTT and 100 uCi $^{32}$P-labeled ATP. Reactions were terminated by blotting onto phosphocellulose paper and washing with 10% phosphoric acid. The % change in fluorescence represents the increase in fluorescence (475 nm excitation, 510 nm emission) observed in each purified protein resulting from incubation

TABLE III

Relative fluorescence, rate of phosphorylation and change in fluorescence upon phosphorylation for phosphorylation sites inserted at the N-terminus

| SEQ ID NO: | Sequence | Relative fluorescence as a % of wild type | Relative rates of phosphorylation | % Change in fluorescence |
|---|---|---|---|---|
| 48 | 1MSKGEELF | 100 | 1.0 | 0 |
| 25 | 1MRKGSCLF | 40 | 5.1 | 5.7 |
| 26 | 1MRKGSLLF | 52 | 1.6 | 8.0 |
| 27 | 1MRRESLLF | 30 | 3.0 | 6.0 |
| 28 | 1MRRDSCLF | 27 | 3.7 | 17 |
| 29 | 1MSRRDSCF | 43 | 2.1 | 25 |
| 30 | 1MSKRRDSL | 7 | 5.5 | 5.1 |

Numbers prior to the sequence indicate amino acid position in wild type GFP where phosphorylation site starts. The relative rates of phosphorylation compare the rate of phosphorylation of the given phosphorylation site with the endogenous protein kinase A phosphorylation site in Aequorea GFP (HKFSV) (SEQ ID NO:45) measured by incorporation of $^{32}$P after incubation of the purified substrate and protein kinase A catalytic subunit in the presence of $^{32}$P-labelled ATP using the standard protocols described earlier. The % change in fluorescence represents the change in fluorescence (488 nm excitation, 511 nm emission) observed in each purified protein as a result of incubation with excess protein kinase A catalytic subunit for 1 hour at 30° C. using phosphorylation conditions described earlier.

These results demonstrated that mutants whose sequence closely resembles the native protein retain considerable fluorescence, display good kinetics of phosphorylation, but show relatively small changes in fluorescence after phosphorylation. To improve the effect of phosphorylation on fluorescence, amino acids around the phosphorylation site were mutated to create an optimal phosphorylation sequence even if it disordered the existing local tertiary structure. Such disruption was predicted and found to decrease the basal fluorescence of these constructs in their non-phosphorylated state (Table IV).

TABLE IV

Relative fluorescence before phosphorylation and change in fluorescence upon phosphorylation for more drastically altered phosphorylation sites inserted at the N-terminus

| SEQ ID NO: | Sequence | Relative fluorescence as a % of wild-type | % Change in fluorescence upon phosphorylation |
|---|---|---|---|
| 48 | 1MSKGEELF (=WT) | =100 | 0 |
| 31 | 1MSRRRRSI | 5.8 | 40 |
| 32 | 1MRRRRSII | 5.1 | 70 |
| 33 | −1MRRRRSIII | n.d. | 43 |
| 34 | −2MRRRRSIIIF | 0.7 | 15 |
| 35 | −3MRRRRSIIIIF | 0.6 | 70 |

Numbers prior to the sequence indicate amino acid position in wild type GFP where phosphorylation site starts. Negative numbers indicate extensions onto the wild-type N-terminus. The % change in fluorescence represents the change in fluorescence (488 excitation, 511 emission) observed in each purified protein resulting from incubation with excess protein kinase A catalytic subunit for 1 hour at 30° C. using standard phosphorylation conditions described earlier.

Perhaps because of the reduced basal fluorescence, phosphorylation by protein kinase A produced greater percentage increases in fluorescence in these constructs than in the more conservative mutations of Table II. Constructs 1MRRRRSII (SEQ ID NO:32) and −3MRRRRSIIIIF (SEQ ID NO:35) displayed the greatest increases, about 70%, in fluorescence upon phosphorylation using the standard conditions, as shown in FIG. 6. However, these increased percentage increases were obtained at the cost of a reduced ability to fold at higher temperatures and relatively poor fluorescence even after phosphorylation. To improve these characteristics, these mutants were further optimized by additional random mutagenesis with a novel selection procedure.

C. Further optimization of N-terminal phosphorylation sites by random mutagenesis of the remainder of GFP The two best constructs from above (1MRRRRSII (SEQ ID NO:32) and −3MRRRRSIII IF (SEQ ID NO:35)) were further mutagenized and screened for variants that are highly fluorescent when phosphorylated, but weakly fluorescent when non-phosphorylated. The method involved expression of a randomly mutated fluorescent substrate with or without simultaneous co-expression of the constitutively active catalytic subunit of protein kinase A in bacteria, and screening the individual mutants to determine those that are highly fluorescent in the presence but not the absence of the kinase.

Figure 7:
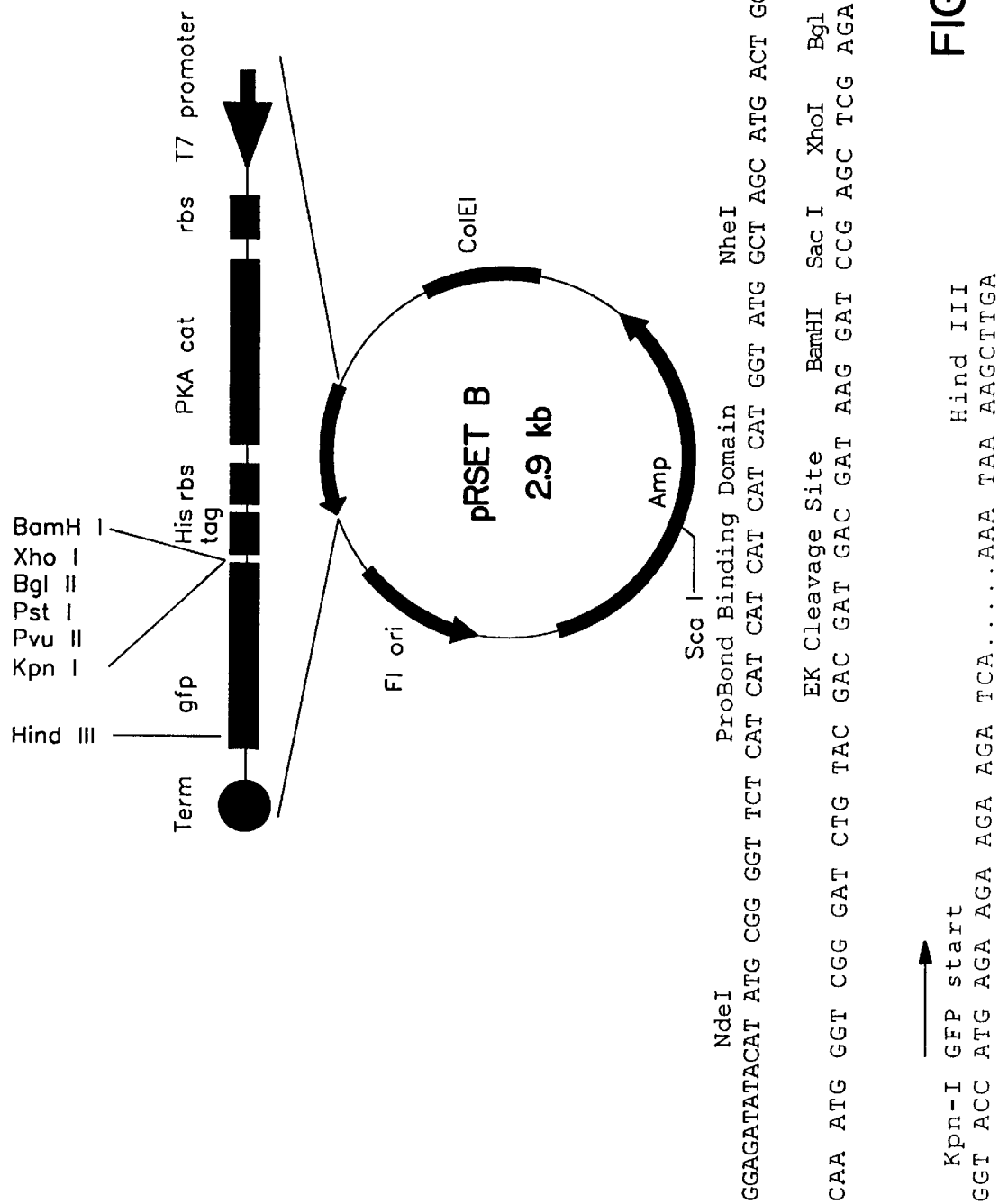
FIG. 7 depicts an expression vector having expression control sequences operably linked to sequences coding for the expression of protein kinase A catalytic subunit (PKA cat) upstream from sequences coding for the expression of a fluorescent protein substrate (nucleotide=SEQ ID NO:41 and SEQ ID NO:42).

To enable co-expression of the kinase and potential substrates, a new expression vector with the kinase C subunit upstream from the fluorescent substrate was constructed (FIG. 7). Random mutations were introduced into GFP by error-prone PCR and the resulting population of mutants cloned into the co-expression vector using the appropriate restriction sites. The expression vector containing the mutated fluorescent substrates were transformed into host bacteria and individual bacterial colonies (each derived from a single cell, and hence containing a single unique mutant fluorescent substrate) were grown up.

The colonies were screened for fluorescence either by fluorescence-activated cell sorting (FIG. 8) or by observation under a microscope. Those that exhibited the greatest fluorescence were re-screened under conditions in which the kinase gene was inactivated. This was achieved in either of two ways. In the first method the co-expression vector was isolated and treated with restriction endonucleases and modifying enzymes (EcoR1, klenow fragment and T4 DNA ligase) to cut the kinase gene, add additional bases and relegate the DNA, causing a frame shift and hence inactivating the gene. The treated and non-treated plasmids were then re-transformed into bacteria and compared in fluorescence. Alternatively the plasmids were initially grown in a RecA$^-$ (recombinase A negative) bacterial strain, where the kinase is stable, to screen for brighter mutants in the presence of the kinase. The plasmid DNA was then isolated and re-transformed into a strain of bacteria which is RecA$^+$, in which the kinase is unstable and is lost through homologous recombination of the tandomly repeated ribosome binding sites (rbs). The bacteria have a strong tendency to eliminate the kinase C subunit because it slows their multiplication, so cells that splice out the kinase by recombination have a large growth advantage.

Comparison of the brightness of the mutant first in the presence of kinase then in its absence indicates the relative effect of phosphorylation on the mutant GFP fluorescence (after normalizing for GFP expression levels). A library of approximately 2×10$^6$ members was screened by this approach. Approximately 500 displayed higher levels of fluorescence when screened in the presence of the kinase. After inactivation of the kinase, one mutant out of the 500 displayed reduced levels of fluorescence. The increased fluorescence of the remainder of the 500 mutants was independent of the presence of the kinase. This mutant GFP was isolated and sequenced and found to contain the following mutations compared to wild-type GFP (FIG. 3, SEQ ID NO:2) (in addition to the N-terminal phosphorylation site 1MRRRRSII (SEQ ID NO:32)): S65A, N149K, V163A and I167T.

Figure 8:
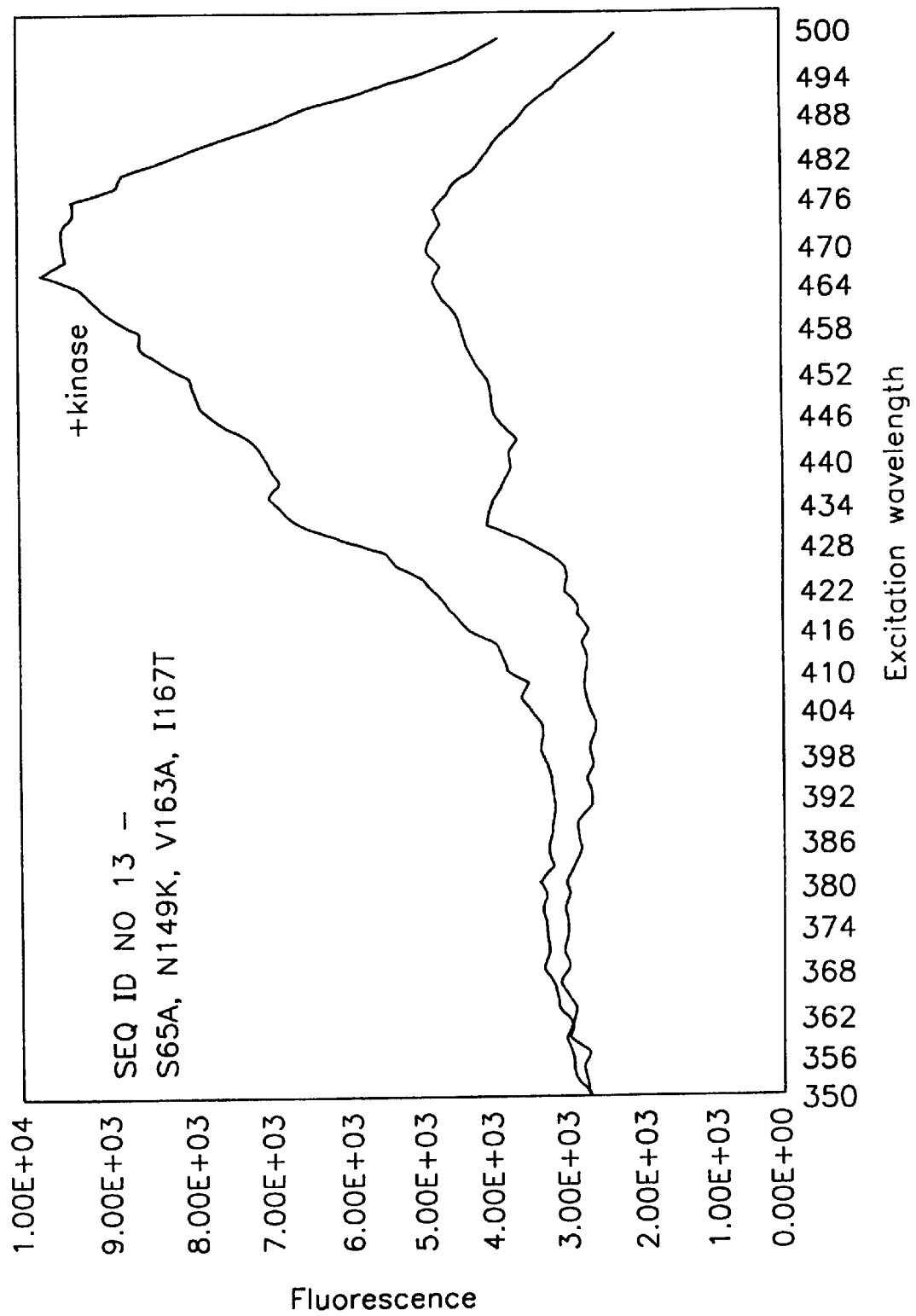
FIG. 8 depicts the fluorescence excitation spectrum of 1MRRRRSII (SEQ ID NO:33): S65A, N149K, V163A and I167T before and after phosphorylation by protein kinase A using standard phosphorylation conditions. The spectrum after phosphorylation has higher amplitude than the spectrum before phosphorylation.

To confirm that this mutant was indeed directly sensitive to protein kinase A phosphorylation and to quantify its responsively, it was expressed in the absence of kinase. The E. coli were lysed and the protein purified as described earlier using a nickel affinity column. The protein exhibited high levels of fluorescence when induced at 30° C. but displayed reduced fluorescence when incubated at 37° C. After such preincubation (37° C. overnight) and separation of the less fluorescent material by centrifugation, this protein exhibited the largest change in fluorescence upon phosphorylation yet observed (FIG. 8). The tolerance of this mutant for 37° C. treatment suggests that this mutant is suitable for use in mammalian cells.

The present invention provides novel assays for protein kinase activity involving novel fluorescent protein substrates. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted.

What is claimed is:

1. A polynucleotide, comprising
   a nucleic acid molecule encoding an Aequorea-related fluorescent protein comprising a phosphorylation site for a protein kinase within ten amino acids of the amino terminus of said Aequorea-related fluorescent protein,
   wherein said Aequorea-related fluorescent protein exhibits a different fluorescent property in the phosphorylated state than in the un-phosphorylated state.

2. The polynucleotide of claim 1,
   wherein said phosphorylation site for a protein kinase is for a protein kinase A, a cGMP-dependent protein kinase, a protein kinase C, a $Ca^{2+}$/calmodulin-dependent protein kinase I, a $Ca^{2+}$/calmodulin-dependent protein kinase II or a MAP kinase activated protein kinase type 1.

3. The polynucleotide of claim 1,
   wherein said phosphorylation site for a protein kinase is RRXSZ (SEQ ID NO:3); RRXTZ (SEQ ID NO:4), wherein X is any amino acid and Z is a hydrophobic amino acid; BKISASEFDR PLR (SEQ ID NO:5), where B represents either lysine (K) or arginine (R), and the first S is the site of phosphorylation; XRXX-SXRX (SEQ ID NO:7), wherein X is any amino acid; KKKKRFSFK (SEQ ID NO.8); LRRLSDSNF (SEQ ID NO 9); KKLNRTLTVA (SEQ ID NO: 10); or KKANRTLSVA (SEQ ID NO:11).

4. The polynucleotide of claim 1,
   wherein said Aequorea-related fluorescent protein is P4, P4-3, W7, W2, S65T, P4-1, S65A, S65L, Y66F or Y66W.

5. The polynucleotide of claim 1,
   wherein said Aequorea-related fluorescent protein comprises a substitution at S65.

6. The polynucleotide of claim 1,
   wherein said Aequorea-related fluorescent protein comprises a substitution at Y66.

7. The polynucleotide of claim 1,
   wherein said Aequorea-related fluorescent protein comprises a folding mutation.

8. The polynucleotide of claim 1,
   wherein said phosphorylation site for a protein kinase is contained within the sequence MRRRRSIITG (SEQ ID NO: 12) or MRRRRSII IIFTG (SEQ ID NO:13).

9. The polynucleotide of claim 1,
   wherein said Aequorea-related fluorescent protein comprises a substitution selected from the group consisting of S65A, N149K, V163A and I167T.

10. The polynucleotide of claim 2,
wherein said phosphorylation site for a protein kinase is for a protein kinase A.

11. The polynucleotide of claim 2,
wherein said phosphorylation site for a protein kinase is for a cGMP-dependent protein kinase.

12. The polynucleotide of claim 2,
wherein said phosphorylation site for a protein kinase is for a protein kinase C.

13. The polynucleotide of claim 2,
wherein said phosphorylation site for a protein kinase is for a $Ca^{2+}$/calmodulin-dependent protein kinase I.

14. The polynucleotide of claim 2,
wherein said phosphorylation site for a protein kinase is for a $Ca^{2+}$/calmodulin-dependent protein kinase II.

15. The polynucleotide of claim 2,
wherein said phosphorylation site for a protein kinase is for a MAP kinase activated protein kinase type 1.

16. A polynucleotide, comprising:
a nucleic acid encoding an Aequorea-related fluorescent protein with at least a contiguous sequence of 200 amino acids having at least 95% identity with the amino acid sequence of SEQ ID NO:2,
wherein said Aequorea-related fluorescent protein is modified within ten amino acids of its amino-terminus by insertion of a phosphorylation site for a protein kinase, and
further wherein said Aequorea-related fluorescent protein exhibits a different fluorescent property in the phosphorylated state than in the unphosphorylated state.

17. The polynucleotide of claim 16,
wherein said phosphorylation site for a protein kinase is for a protein kinase A, a cGMP-dependent protein kinase, a protein kinase C, a $Ca^{2+}$/calmodulin-dependent protein kinase I, a $Ca^{2+}$/calmodulin-dependent protein kinase II or a MAP kinase activated protein kinase type 1.

18. The polynucleotide of claim 16,
wherein said Aequorea-related fluorescent protein comprises a mutation at S65 or Y66.

19. The polynucleotide of claim 16,
wherein said Aequorea-related fluorescent protein comprises a folding mutation.

20. The polynucleotide of claim 16,
wherein said Aequorea-related fluorescent protein comprises the substitution N149K.

21. The polynucleotide of claim 16,
wherein said Aequorea-related fluorescent protein comprises the substitution V163A.

22. The polynucleotide of claim 16,
wherein said Aequorea-related fluorescent protein comprises the substitution I167T.

23. A host cell, comprising:
a recombinant nucleic acid molecule, said recombinant nucleic acid molecule comprising expression control sequences operatively linked to a nucleic acid sequence encoding an Aequorea-related fluorescent protein,
wherein said Aequorea-related fluorescent protein comprises a phosphorylation site for a protein kinase within ten amino acids of its amino terminus,
wherein said Aequorea-related fluorescent protein exhibits a different fluorescent property in the phosphorylated state than in the unphosphorylated state.

\* \* \* \* \*

SEQUENCE LISTING (1) GENERAL INFORMATION:

(iii) NUMBER OF SEQUENCES: 48

(2) INFORMATION FOR SEQ ID NO:1:

(i) SEQUENCE CHARACTERISTICS:
      (A) LENGTH: 717 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: CDS
      (B) LOCATION: 1..717
      (D) OTHER INFORMATION: /product= "wild-type Aequorea green
          fluorescent protein (GFP)"

(xi) SEQUENCE DESCRIPTION: SEQ ID NO:1:

```
ATG AGT AAA GGA GAA GAA CTT TTC ACT GGA GTT GTC CCA ATT CTT GTT      48
Met Ser Lys Gly Glu Glu Leu Phe Thr Gly Val Val Pro Ile Leu Val
 1               5                  10                  15

GAA TTA GAT GGT GAT GTT AAT GGG CAC AAA TTT TCT GTC AGT GGA GAG      96
Glu Leu Asp Gly Asp Val Asn Gly His Lys Phe Ser Val Ser Gly Glu
             20                  25                  30

GGT GAA GGT GAT GCA ACA TAC GGA AAA CTT ACC CTT AAA TTT ATT TGC     144
Gly Glu Gly Asp Ala Thr Tyr Gly Lys Leu Thr Leu Lys Phe Ile Cys
         35                  40                  45

ACT ACT GGA AAA CTA CCT GTT CCA TGG CCA ACA CTT GTC ACT ACT TTC     192
Thr Thr Gly Lys Leu Pro Val Pro Trp Pro Thr Leu Val Thr Thr Phe
     50                  55                  60

TCT TAT GGT GTT CAA TGC TTT TCA AGA TAC CCA GAT CAT ATG AAA CGG     240
Ser Tyr Gly Val Gln Cys Phe Ser Arg Tyr Pro Asp His Met Lys Arg
 65                  70                  75                  80

CAT GAC TTT TTC AAG AGT GCC ATG CCC GAA GGT TAT GTA CAG GAA AGA     288
His Asp Phe Phe Lys Ser Ala Met Pro Glu Gly Tyr Val Gln Glu Arg
                 85                  90                  95

ACT ATA TTT TTC AAA GAT GAC GGG AAC TAC AAG ACA CGT GCT GAA GTC     336
Thr Ile Phe Phe Lys Asp Asp Gly Asn Tyr Lys Thr Arg Ala Glu Val
            100                 105                 110

AAG TTT GAA GGT GAT ACC CTT GTT AAT AGA ATC GAG TTA AAA GGT ATT     384
Lys Phe Glu Gly Asp Thr Leu Val Asn Arg Ile Glu Leu Lys Gly Ile
        115                 120                 125

GAT TTT AAA GAA GAT GGA AAC ATT CTT GGA CAC AAA TTG GAA TAC AAC     432
Asp Phe Lys Glu Asp Gly Asn Ile Leu Gly His Lys Leu Glu Tyr Asn
    130                 135                 140

TAT AAC TCA CAC AAT GTA TAC ATC ATG GCA GAC AAA CAA AAG AAT GGA     480
Tyr Asn Ser His Asn Val Tyr Ile Met Ala Asp Lys Gln Lys Asn Gly
145                 150                 155                 160

ATC AAA GTT AAC TTC AAA ATT AGA CAC AAC ATT GAA GAT GGA AGC GTT     528
Ile Lys Val Asn Phe Lys Ile Arg His Asn Ile Glu Asp Gly Ser Val
```

```
                     165                 170                 175
CAA CTA GCA GAC CAT TAT CAA CAA AAT ACT CCA ATT GGC GAT GGC CCT          576
Gln Leu Ala Asp His Tyr Gln Gln Asn Thr Pro Ile Gly Asp Gly Pro
            180                 185                 190

GTC CTT TTA CCA GAC AAC CAT TAC CTG TCC ACA CAA TCT GCC CTT TCG          624
Val Leu Leu Pro Asp Asn His Tyr Leu Ser Thr Gln Ser Ala Leu Ser
        195                 200                 205

AAA GAT CCC AAC GAA AAG AGA GAC CAC ATG GTC CTT CTT GAG TTT GTA          672
Lys Asp Pro Asn Glu Lys Arg Asp His Met Val Leu Leu Glu Phe Val
    210                 215                 220

ACA GCT GCT GGG ATT ACA CAT GGC ATG GAT GAA CTA TAC AAA                  714
Thr Ala Ala Gly Ile Thr His Gly Met Asp Glu Leu Tyr Lys
225                 230                 235

TAA                                                                      717
```

(2) INFORMATION FOR SEQ ID NO:2:

(i) SEQUENCE CHARACTERISTICS:
        (A) LENGTH: 238 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ser Lys Gly Glu Glu Leu Phe Thr Gly Val Val Pro Ile Leu Val
 1               5                  10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

(2) INFORMATION FOR SEQ ID NO:3:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 2
            (D) OTHER INFORMATION: /product= "OTHER"
                /note= "Xaa = preferably Arg, may be
                Lys"

(ix) FEATURE:
            (A) NAME/KEY: Modified-site
            (B) LOCATION: 3
            (D) OTHER INFORMATION: /product= "OTHER"
                /note= "Xaa = any amino acid"

(ix) FEATURE:
            (A) NAME/KEY: Modified-site
            (B) LOCATION: 5
            (D) OTHER INFORMATION: /product= "OTHER"
                /note= "Xaa = hydrophobic amino acid,
                preferably Val, Leu or Ile"

(xi) SEQUENCE DESCRIPTION: SEQ ID NO:3:

Arg Xaa Xaa Ser Xaa
1               5

(2) INFORMATION FOR SEQ ID NO:4:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 2
            (D) OTHER INFORMATION: /product= "OTHER"
                /note= "Xaa = preferably Arg, may be
                Lys"

(ix) FEATURE:
            (A) NAME/KEY: Modified-site
            (B) LOCATION: 3
            (D) OTHER INFORMATION: /product= "OTHER"
                /note= "Xaa = any amino acid"

(ix) FEATURE:
            (A) NAME/KEY: Modified-site
            (B) LOCATION: 5
            (D) OTHER INFORMATION: /product= "OTHER"
                /note= "Xaa = hydrophobic amino acid,
                preferably Val, Leu or Ile"

(xi) SEQUENCE DESCRIPTION: SEQ ID NO:4:

Arg Xaa Xaa Thr Xaa
1               5

(2) INFORMATION FOR SEQ ID NO:5:

(i) SEQUENCE CHARACTERISTICS:
            (A) LENGTH: 13 amino acids
            (B) TYPE: amino acid
            (C) STRANDEDNESS:
            (D) TOPOLOGY: linear (ii) MOLECULE TYPE: peptide -continued

```
    (ix) FEATURE:
         (A) NAME/KEY: Modified-site
         (B) LOCATION: 1
         (D) OTHER INFORMATION: /product= "OTHER"
             /note= "Xaa = Lys or Arg"

(xi) SEQUENCE DESCRIPTION: SEQ ID NO:5:

Xaa Lys Ile Ser Ala Ser Glu Phe Asp Arg Pro Leu Arg
1               5                  10

(2) INFORMATION FOR SEQ ID NO:6:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

Asp Arg Pro Leu Arg
1               5

(2) INFORMATION FOR SEQ ID NO:7:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

Xaa Arg Xaa Xaa Ser Xaa Arg Xaa
1               5

(2) INFORMATION FOR SEQ ID NO:8:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

Lys Lys Lys Lys Arg Phe Ser Phe Lys
1               5

(2) INFORMATION FOR SEQ ID NO:9:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

Leu Arg Arg Leu Ser Asp Ser Asn Phe
1               5

(2) INFORMATION FOR SEQ ID NO:10:

(i) SEQUENCE CHARACTERISTICS:
        (A) LENGTH: 10 amino acids
```

(B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

Lys Lys Leu Asn Arg Thr Leu Thr Val Ala
1               5                   10

(2) INFORMATION FOR SEQ ID NO:11:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

Lys Lys Ala Asn Arg Thr Leu Ser Val Ala
1               5                   10

(2) INFORMATION FOR SEQ ID NO:12:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:12:

Met Arg Arg Arg Arg Ser Ile Ile Thr Gly
1               5                   10

(2) INFORMATION FOR SEQ ID NO:13:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

Met Arg Arg Arg Arg Ser Ile Ile Ile Ile Phe Thr Gly
1               5                   10

(2) INFORMATION FOR SEQ ID NO:14:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:14:

Arg Arg Phe Ser Ala
1               5

(2) INFORMATION FOR SEQ ID NO:15:

(i) SEQUENCE CHARACTERISTICS:
        (A) LENGTH: 5 amino acids (B) TYPE: amino acid
                (C) STRANDEDNESS:
                (D) TOPOLOGY: linear (ii) MOLECULE TYPE: peptide (xi) SEQUENCE DESCRIPTION: SEQ ID NO:15:

Lys Arg Asp Ser Met
1               5

(2) INFORMATION FOR SEQ ID NO:16:

(i) SEQUENCE CHARACTERISTICS:
                (A) LENGTH: 9 amino acids
                (B) TYPE: amino acid
                (C) STRANDEDNESS:
                (D) TOPOLOGY: linear (ii) MOLECULE TYPE: peptide (xi) SEQUENCE DESCRIPTION: SEQ ID NO:16:

Met Ser Lys Arg Arg Asp Ser Leu Thr
1               5

(2) INFORMATION FOR SEQ ID NO:17:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (ii) MOLECULE TYPE: DNA (xi) SEQUENCE DESCRIPTION: SEQ ID NO:17:

NNKNNKNNKN NKNNKNNK                                         18

(2) INFORMATION FOR SEQ ID NO:18:

(i) SEQUENCE CHARACTERISTICS:
                (A) LENGTH: 5 amino acids
                (B) TYPE: amino acid
                (C) STRANDEDNESS:
                (D) TOPOLOGY: linear (ii) MOLECULE TYPE: peptide (xi) SEQUENCE DESCRIPTION: SEQ ID NO:18:

Arg Arg Leu Ser Ile
1               5

(2) INFORMATION FOR SEQ ID NO:19:

(i) SEQUENCE CHARACTERISTICS:
                (A) LENGTH: 5 amino acids
                (B) TYPE: amino acid
                (C) STRANDEDNESS:
                (D) TOPOLOGY: linear (ii) MOLECULE TYPE: peptide (xi) SEQUENCE DESCRIPTION: SEQ ID NO:19:

Arg Arg Phe Ser Val
1               5

(2) INFORMATION FOR SEQ ID NO:20:

(i) SEQUENCE CHARACTERISTICS:
                (A) LENGTH: 5 amino acids
                (B) TYPE: amino acid

```
        (C) STRANDEDNESS:
        (D) TOPOLOGY: linear (ii) MOLECULE TYPE: peptide (xi) SEQUENCE DESCRIPTION: SEQ ID NO:20:

Arg Arg Phe Ser Arg
1               5

(2) INFORMATION FOR SEQ ID NO:21:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:21:

Arg Arg Ser Ile Phe
1               5

(2) INFORMATION FOR SEQ ID NO:22:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:22:

Arg Arg Gly Ser Ile Leu
1               5

(2) INFORMATION FOR SEQ ID NO:23:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:23:

Lys Arg Lys Ser Gly Ile
1               5

(2) INFORMATION FOR SEQ ID NO:24:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:24:

Arg Arg Gly Ser Val
1               5

(2) INFORMATION FOR SEQ ID NO:25:

(i) SEQUENCE CHARACTERISTICS:
        (A) LENGTH: 8 amino acids
        (B) TYPE: amino acid
```

```
            (C) STRANDEDNESS:
            (D) TOPOLOGY: linear (ii) MOLECULE TYPE: peptide (xi) SEQUENCE DESCRIPTION: SEQ ID NO:25:

Met Arg Lys Gly Ser Cys Leu Phe
1               5

(2) INFORMATION FOR SEQ ID NO:26:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:26:

Met Arg Lys Gly Ser Leu Leu Phe
1               5

(2) INFORMATION FOR SEQ ID NO:27:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:27:

Met Arg Arg Glu Ser Leu Leu Phe
1               5

(2) INFORMATION FOR SEQ ID NO:28:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:28:

Met Arg Arg Asp Ser Cys Leu Phe
1               5

(2) INFORMATION FOR SEQ ID NO:29:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:29:

Met Ser Arg Arg Asp Ser Cys Phe
1               5

(2) INFORMATION FOR SEQ ID NO:30:

(i) SEQUENCE CHARACTERISTICS:
            (A) LENGTH: 8 amino acids
            (B) TYPE: amino acid
```

(C) STRANDEDNESS:
            (D) TOPOLOGY: linear (ii) MOLECULE TYPE: peptide (xi) SEQUENCE DESCRIPTION: SEQ ID NO:30:

Met Ser Lys Arg Arg Asp Ser Leu
1               5

(2) INFORMATION FOR SEQ ID NO:31:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:31:

Met Ser Arg Arg Arg Arg Ser Ile
1               5

(2) INFORMATION FOR SEQ ID NO:32:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:32:

Met Arg Arg Arg Arg Ser Ile Ile
1               5

(2) INFORMATION FOR SEQ ID NO:33:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:33:

Met Arg Arg Arg Arg Ser Ile Ile Ile
1               5

(2) INFORMATION FOR SEQ ID NO:34:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:34:

Met Arg Arg Arg Arg Ser Ile Ile Ile Phe
1               5                   10

(2) INFORMATION FOR SEQ ID NO:35:

(i) SEQUENCE CHARACTERISTICS:
            (A) LENGTH: 11 amino acids
            (B) TYPE: amino acid (C) STRANDEDNESS:
(D) TOPOLOGY: linear (ii) MOLECULE TYPE: peptide (xi) SEQUENCE DESCRIPTION: SEQ ID NO:35:

Met Arg Arg Arg Arg Ser Ile Ile Ile Ile Phe
1               5                   10

(2) INFORMATION FOR SEQ ID NO:36:

(i) SEQUENCE CHARACTERISTICS:
    (A) LENGTH: 717 base pairs
    (B) TYPE: nucleic acid
    (C) STRANDEDNESS: single
    (D) TOPOLOGY: linear (ii) MOLECULE TYPE: DNA (ix) FEATURE:
    (A) NAME/KEY: CDS
    (B) LOCATION: 1..717
    (D) OTHER INFORMATION: /product= "phosphorylation mutant of
        Aequorea green fluorescent protein
    (GPF)"

(xi) SEQUENCE DESCRIPTION: SEQ ID NO:36:

| | | | | | | | | | | | | | | | |
|---|---|---|---|---|---|---|---|---|---|---|---|---|---|---|---|
| ATG | AGT | AAA | GGA | GAA | GAA | CTT | TTC | ACT | GGA | GTT | GTC | CCA | ATT | CTT | GTT | 48 |
| Met | Ser | Lys | Gly | Glu | Glu | Leu | Phe | Thr | Gly | Val | Val | Pro | Ile | Leu | Val |
| 1 | | | | 5 | | | | | 10 | | | | | 15 | |

| GAA | TTA | GAT | GGT | GAT | GTT | AAT | GGG | AGA | AGA | TTT | TCT | GTC | AGT | GGA | GAG | 96 |
|---|---|---|---|---|---|---|---|---|---|---|---|---|---|---|---|---|
| Glu | Leu | Asp | Gly | Asp | Val | Asn | Gly | Arg | Arg | Phe | Ser | Val | Ser | Gly | Glu |
| | | | 20 | | | | | 25 | | | | | 30 | | |

| GGT | GAA | GGT | GAT | GCA | ACA | TAC | GGA | AAA | CTT | ACC | CTT | AAA | TTT | ATT | TGC | 144 |
|---|---|---|---|---|---|---|---|---|---|---|---|---|---|---|---|---|
| Gly | Glu | Gly | Asp | Ala | Thr | Tyr | Gly | Lys | Leu | Thr | Leu | Lys | Phe | Ile | Cys |
| | | | 35 | | | | | 40 | | | | | 45 | | |

| ACT | ACT | GGA | AAA | CTA | CCT | GTT | CCA | TGG | CCA | ACA | CTT | GTC | ACT | ACT | TTC | 192 |
|---|---|---|---|---|---|---|---|---|---|---|---|---|---|---|---|---|
| Thr | Thr | Gly | Lys | Leu | Pro | Val | Pro | Trp | Pro | Thr | Leu | Val | Thr | Thr | Phe |
| | 50 | | | | | 55 | | | | | 60 | | | | |

| TCT | TAT | GGT | GTT | AGA | AGA | TTT | TCA | GCA | TAC | CCA | GAT | CAT | ATG | AAA | CGG | 240 |
|---|---|---|---|---|---|---|---|---|---|---|---|---|---|---|---|---|
| Ser | Tyr | Gly | Val | Arg | Arg | Phe | Ser | Ala | Tyr | Pro | Asp | His | Met | Lys | Arg |
| 65 | | | | | 70 | | | | | 75 | | | | | 80 |

| CAT | GAC | TTT | TTC | AAG | AGT | GCC | ATG | CCC | GAA | GGT | TAT | GTA | CAG | AGA | AGA | 288 |
|---|---|---|---|---|---|---|---|---|---|---|---|---|---|---|---|---|
| His | Asp | Phe | Phe | Lys | Ser | Ala | Met | Pro | Glu | Gly | Tyr | Val | Gln | Arg | Arg |
| | | | | 85 | | | | | 90 | | | | | 95 | |

| TCT | ATA | TTT | TTC | AAA | GAT | GAC | GGG | AAC | TAC | AAG | ACA | CGT | GCT | GAA | GTC | 336 |
|---|---|---|---|---|---|---|---|---|---|---|---|---|---|---|---|---|
| Ser | Ile | Phe | Phe | Lys | Asp | Asp | Gly | Asn | Tyr | Lys | Thr | Arg | Ala | Glu | Val |
| | | | | 100 | | | | | 105 | | | | | 110 | |

| AAG | TTT | GAA | GGT | GAT | ACC | CTT | GTT | AAT | AGA | ATC | GAG | TTA | AAA | GGT | ATT | 384 |
|---|---|---|---|---|---|---|---|---|---|---|---|---|---|---|---|---|
| Lys | Phe | Glu | Gly | Asp | Thr | Leu | Val | Asn | Arg | Ile | Glu | Leu | Lys | Gly | Ile |
| | | | | 115 | | | | | 120 | | | | | 125 | |

| GAT | TTT | AAA | AGA | AGA | GGA | TCC | ATT | CTT | GGA | CAC | AAA | TTG | GAA | TAC | AAC | 432 |
|---|---|---|---|---|---|---|---|---|---|---|---|---|---|---|---|---|
| Asp | Phe | Lys | Arg | Arg | Gly | Ser | Ile | Leu | Gly | His | Lys | Leu | Glu | Tyr | Asn |
| | 130 | | | | | 135 | | | | | 140 | | | | |

| TAT | AAC | TCA | CAC | AAT | GTA | TAC | ATC | ATG | GCA | GAC | AAA | AGA | AAG | TCT | GGA | 480 |
|---|---|---|---|---|---|---|---|---|---|---|---|---|---|---|---|---|
| Tyr | Asn | Ser | His | Asn | Val | Tyr | Ile | Met | Ala | Asp | Lys | Arg | Lys | Ser | Gly |
| 145 | | | | | 150 | | | | | 155 | | | | | 160 |

| ATC | AAA | GTT | AAC | TTC | AAA | ATT | AGA | CAC | AAC | ATT | AGA | AGA | GGA | AGC | GTT | 528 |
|---|---|---|---|---|---|---|---|---|---|---|---|---|---|---|---|---|
| Ile | Lys | Val | Asn | Phe | Lys | Ile | Arg | His | Asn | Ile | Arg | Arg | Gly | Ser | Val |
| | | | | 165 | | | | | 170 | | | | | 175 | |

| CAA | CTA | GCA | GAC | CAT | TAT | CAA | CAA | AAT | ACT | CCA | ATT | GGC | GAT | GGC | CCT | 576 |
|---|---|---|---|---|---|---|---|---|---|---|---|---|---|---|---|---|
| Gln | Leu | Ala | Asp | His | Tyr | Gln | Gln | Asn | Thr | Pro | Ile | Gly | Asp | Gly | Pro |
| | | | 180 | | | | | 185 | | | | | 190 | | |

| GTC | CTT | TTA | CCA | GAC | AAC | AGA | AGA | CTG | TCC | ATA | CAA | TCT | GCC | CTT | TCG | 624 |
|---|---|---|---|---|---|---|---|---|---|---|---|---|---|---|---|---|
| Val | Leu | Leu | Pro | Asp | Asn | Arg | Arg | Leu | Ser | Ile | Gln | Ser | Ala | Leu | Ser |

```
                195                 200                 205
AAA GAT CCC AAC GAA AAG AGA GAC AGA ATG GTC CTT CTT GAG TTT GTA    672
Lys Asp Pro Asn Glu Lys Arg Asp Arg Met Val Leu Leu Glu Phe Val
210                 215                 220

ACA GCT GCT GGG ATT ACA CAT GGC ATG GAT GAA CTA TAC AAA            714
Thr Ala Ala Gly Ile Thr His Gly Met Asp Glu Leu Tyr Lys
225                 230                 235

TAA                                                                717
```

(2) INFORMATION FOR SEQ ID NO:37:

(i) SEQUENCE CHARACTERISTICS:
        (A) LENGTH: 238 amino acids
        (B) TYPE: amino acid
        (D) TOPOLOGY: linear (ii) MOLECULE TYPE: protein (xi) SEQUENCE DESCRIPTION: SEQ ID NO:37:

```
Met Ser Lys Gly Glu Glu Leu Phe Thr Gly Val Val Pro Ile Leu Val
1               5                   10                  15

Glu Leu Asp Gly Asp Val Asn Gly Arg Arg Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Arg Arg Phe Ser Ala Tyr Pro Asp His Met Lys Arg
65                  70                  75                  80

His Asp Phe Phe Lys Ser Ala Met Pro Glu Gly Tyr Val Gln Arg Arg
                85                  90                  95

Ser Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Arg Arg Gly Ser Ile Leu Gly His Lys Leu Glu Tyr Asn
    130                 135                 140

Tyr Asn Ser His Asn Val Tyr Ile Met Ala Asp Lys Arg Lys Ser Gly
145                 150                 155                 160

Ile Lys Val Asn Phe Lys Ile Arg His Asn Ile Arg Arg Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn Arg Arg Leu Ser Ile Gln Ser Ala Leu Ser
        195                 200                 205

Lys Asp Pro Asn Glu Lys Arg Asp Arg Met Val Leu Leu Glu Phe Val
    210                 215                 220

Thr Ala Ala Gly Ile Thr His Gly Met Asp Glu Leu Tyr Lys
225                 230                 235
```

(2) INFORMATION FOR SEQ ID NO:38:

(i) SEQUENCE CHARACTERISTICS:
        (A) LENGTH: 129 base pairs
        (B) TYPE: nucleic acid
        (C) STRANDEDNESS: single
        (D) TOPOLOGY: linear (ii) MOLECULE TYPE: DNA (ix) FEATURE:
              (A) NAME/KEY: CDS
              (B) LOCATION: 13..129

(xi) SEQUENCE DESCRIPTION: SEQ ID NO:38:

```
GGAGATATAC AT ATG CGG GGT TCT CAT CAT CAT CAT CAT CAT GGT ATG        48
              Met Arg Gly Ser His His His His His His Gly Met
                1               5                  10

GCT AGC ATG ACT GGT GGA CAG CAA ATG GGT CGG GAT CTG TAC GAC GAT      96
Ala Ser Met Thr Gly Gly Gln Gln Met Gly Arg Asp Leu Tyr Asp Asp
         15                  20                  25

GAC GAT AAG GAT CCC CCC GCT GAA TTC ATG AGT                         129
Asp Asp Lys Asp Pro Pro Ala Glu Phe Met Ser
     30                  35
```

(2) INFORMATION FOR SEQ ID NO:39:

(i) SEQUENCE CHARACTERISTICS:
              (A) LENGTH: 39 amino acids
              (B) TYPE: amino acid
              (D) TOPOLOGY: linear (ii) MOLECULE TYPE: protein (xi) SEQUENCE DESCRIPTION: SEQ ID NO:39:

```
Met Arg Gly Ser His His His His His His Gly Met Ala Ser Met Thr
  1               5                  10                  15

Gly Gly Gln Gln Met Gly Arg Asp Leu Tyr Asp Asp Asp Lys Asp
             20                  25                  30

Pro Pro Ala Glu Phe Met Ser
         35
```

(2) INFORMATION FOR SEQ ID NO:40:

(i) SEQUENCE CHARACTERISTICS:
              (A) LENGTH: 61 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:40:

```
TACAAATAAT AAGGATCCGA GCTCGAGATC TGCAGCTGGT ACCATGGAAT TCGAAGGTGG    60
A                                                                    61
```

(2) INFORMATION FOR SEQ ID NO:41:

(i) SEQUENCE CHARACTERISTICS:
              (A) LENGTH: 153 base pairs
              (B) TYPE: nucleic acid
              (C) STRANDEDNESS: single
              (D) TOPOLOGY: linear (ii) MOLECULE TYPE: DNA (xi) SEQUENCE DESCRIPTION: SEQ ID NO:41:

```
GGAGATATAC ATATGCGGGG TTCTCATCAT CATCATCATC ATGGTATGGC TAGCATGACT    60
GGTGGACAGC AAATGGGTCG GGATCTGTAC GACGATGACG ATAAGGATCC GAGCTCGAGA   120
TCTGCAGCTG GTACCATGAG AAGAAGAAGA TCA                                153
```

(2) INFORMATION FOR SEQ ID NO:42:

(i) SEQUENCE CHARACTERISTICS:
              (A) LENGTH: 14 base pairs (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:42:

AAATAAAAGC TTGA                                                                     14

(2) INFORMATION FOR SEQ ID NO:43:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:43:

Met Ser Lys Gly Glu Glu Leu Phe Thr Gly
1               5                   10

(2) INFORMATION FOR SEQ ID NO:44:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:44:

Met Ser Lys Gly Glu Glu Leu Phe Thr
1               5

(2) INFORMATION FOR SEQ ID NO:45:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:45:

His Lys Phe Ser Val
1               5

(2) INFORMATION FOR SEQ ID NO:46:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 3
            (D) OTHER INFORMATION: /product= "OTHER"
                /note= "Xaa = any amino acid"

(ix) FEATURE:
            (A) NAME/KEY: Modified-site
            (B) LOCATION: 5
            (D) OTHER INFORMATION: /product= "OTHER"
                /note= "Xaa = hydrophobic amino acid"

(xi) SEQUENCE DESCRIPTION: SEQ ID NO:46:

Arg Arg Xaa Ser Xaa
1               5

(2) INFORMATION FOR SEQ ID NO:47:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "OTHER"
            /note= "Xaa = any amino acid"

(ix) FEATURE:
        (A) NAME/KEY: Modified-site
        (B) LOCATION: 5
        (D) OTHER INFORMATION: /product= "OTHER"
            /note= "Xaa = hydrophobic amino acid"

(xi) SEQUENCE DESCRIPTION: SEQ ID NO:47:

Arg Arg Xaa Thr Xaa
1               5

(2) INFORMATION FOR SEQ ID NO:48:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:48:

Met Ser Lys Gly Glu Glu Leu Phe
1               5